(12) United States Patent
Albert et al.

(10) Patent No.: US 7,575,598 B2
(45) Date of Patent: *Aug. 18, 2009

(54) ANTERIOR LUMBAR INTERVERTEBRAL STABILIZER

(75) Inventors: Todd James Albert, Narberth, PA (US); Richard H. Rothman, Philadelphia, PA (US); Rafail Zubok, Midland Park, NJ (US); Mikhail Kvitnitsky, Clifton, NJ (US)

(73) Assignee: Cervical Xpand, LLC, Clifton, NJ (US)

( * ) Notice: Subject to any disclaimer, the term of this patent is extended or adjusted under 35 U.S.C. 154(b) by 178 days.

This patent is subject to a terminal disclaimer.

(21) Appl. No.: 11/176,717

(22) Filed: Jul. 7, 2005

(65) Prior Publication Data

US 2006/0200240 A1  Sep. 7, 2006

Related U.S. Application Data

(60) Provisional application No. 60/658,345, filed on Mar. 3, 2005.

(51) Int. Cl.
*A61F 2/44* (2006.01)
(52) U.S. Cl. ............................... 623/17.13; 623/17.15
(58) Field of Classification Search ................. 606/61, 606/257, 261; 623/17.11–17.16; 267/180
See application file for complete search history.

(56) References Cited

U.S. PATENT DOCUMENTS

| | | | |
|---|---|---|---|
| 4,309,777 A | 1/1982 | Patil | |
| 4,759,769 A | 7/1988 | Hedman et al. | |
| 5,055,104 A | 10/1991 | Ray | |
| 5,263,953 A | 11/1993 | Bagby | |
| 5,306,310 A | 4/1994 | Siebels | |
| 5,320,644 A | 6/1994 | Baumgartner | |
| 5,423,816 A | 6/1995 | Lin | |
| 5,423,817 A | 6/1995 | Lin | |
| 5,458,642 A | 10/1995 | Beer et al. | |
| 5,480,401 A | 1/1996 | Navas | |
| 5,827,328 A | 10/1998 | Buttermann | |
| 6,277,149 B1 * | 8/2001 | Boyle et al. | 623/17.16 |
| 6,296,664 B1 | 10/2001 | Middleton | |

(Continued)

OTHER PUBLICATIONS

Author Peter F. Ullrich, Jr., MD, "Posterior Lumbar Interbody Fusion (PLIF) Surgery", Spine-health.com, Sep. 8, 1999 (Updated Jan. 20, 2004).

(Continued)

*Primary Examiner*—Thomas C Barrett
*Assistant Examiner*—Andrew Yang
(74) *Attorney, Agent, or Firm*—Matthew B. Dernier, Esq.; Gibson & Dernier LLP

(57) ABSTRACT

A lumbar intervertebral stabilizer for a lumbar region of a spine includes: a first surface operable to engage an endplate of a first vertebral bone of a spine; a second surface spaced apart from the first surface and operable to engage an endplate of an adjacent second vertebral bone of the spine; a spring element including at least one of: (i) a helical wound spring; and (ii) a hollow body having at least one slit forming a plurality of annular circumferential helical coils, the spring element being disposed between the first and second surfaces and being operable to provide reactive force in response to compression loads from the first and second vertebral bones, wherein at least some diameters of respective turns of the helical coils differ.

18 Claims, 19 Drawing Sheets

U.S. PATENT DOCUMENTS

| | | | |
|---|---|---|---|
| 6,315,797 B1 | 11/2001 | Middleton | |
| 6,395,035 B2 | 5/2002 | Bresina et al. | |
| 6,440,169 B1 | 8/2002 | Elberg et al. | |
| 6,468,310 B1 | 10/2002 | Ralph et al. | |
| 6,520,996 B1 | 2/2003 | Manasas et al. | |
| 6,572,653 B1 * | 6/2003 | Simonson | 623/17.13 |
| 6,579,321 B1 * | 6/2003 | Gordon et al. | 623/17.16 |
| 6,656,224 B2 | 12/2003 | Middleton | |
| 6,770,094 B2 | 8/2004 | Fehling et al. | |
| 7,052,515 B2 * | 5/2006 | Simonson | 623/17.13 |
| 7,331,994 B2 * | 2/2008 | Gordon et al. | 623/17.13 |
| 2003/0009223 A1 | 1/2003 | Fehling et al. | |
| 2003/0083749 A1 | 5/2003 | Kuslich et al. | |
| 2004/0122517 A1 | 6/2004 | Kuras | |
| 2004/0176842 A1 | 9/2004 | Middleton | |
| 2004/0181285 A1 | 9/2004 | Simonson | |
| 2005/0015150 A1 | 1/2005 | Lee | |
| 2005/0027363 A1 * | 2/2005 | Gordon | 623/17.13 |
| 2005/0043804 A1 | 2/2005 | Gordon et al. | |
| 2005/0060034 A1 * | 3/2005 | Berry et al. | 623/17.11 |
| 2005/0203513 A1 * | 9/2005 | Jahng et al. | 606/61 |
| 2006/0149381 A1 * | 7/2006 | Kim | 623/17.13 |

OTHER PUBLICATIONS

International Search Report for PCT/US05/27506, Jan. 11, 2006, Accin Corporation.

Advertisement: Interspinous Process Distraction (IPD) for treatment of Intermittent Neurogenic Claudication, SFMT Europe B.V., copyright 2003 St. Francis Medical Technologies, Inc. (2 pages).

Transmittal of International Preliminary Report on Patentability and written opinion of the International Search Authority for International Application PCT/US2005/027506.

* cited by examiner

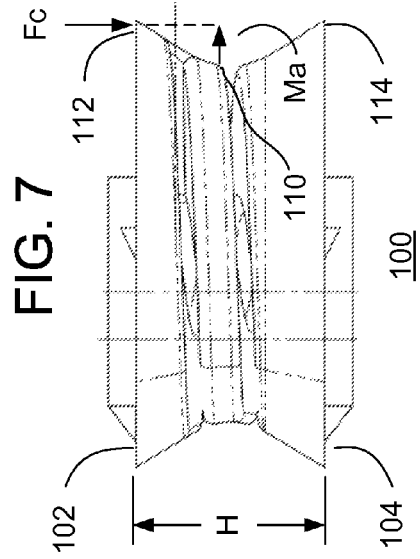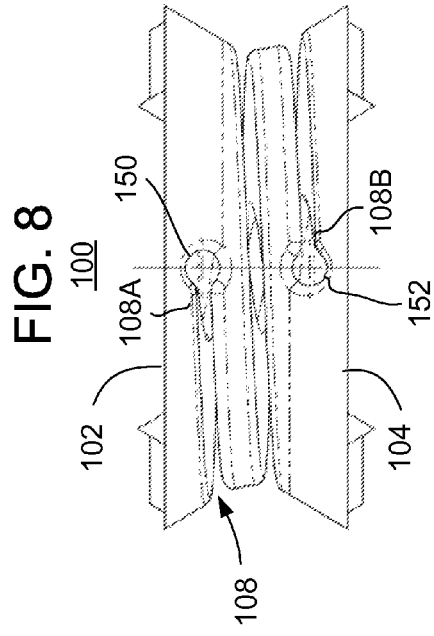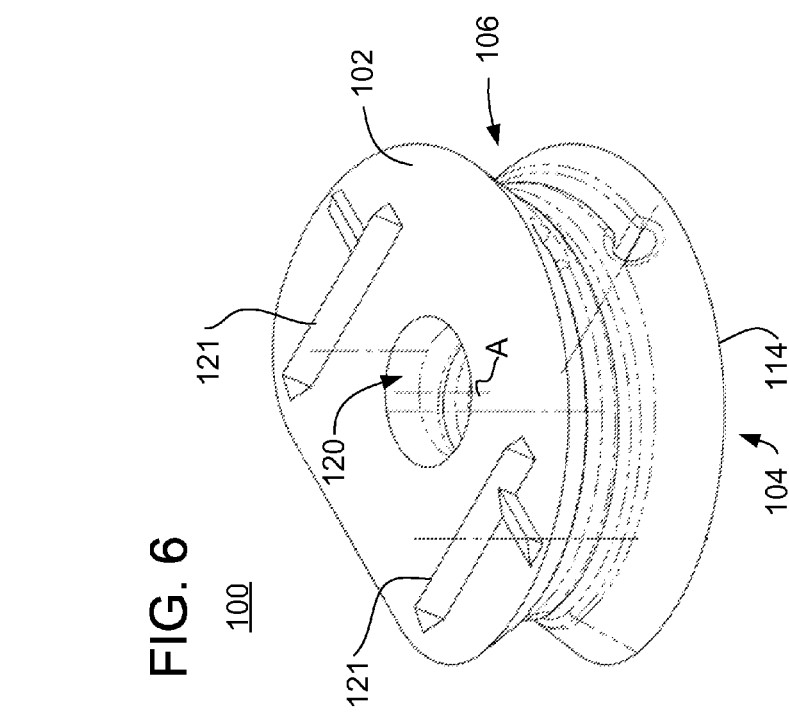

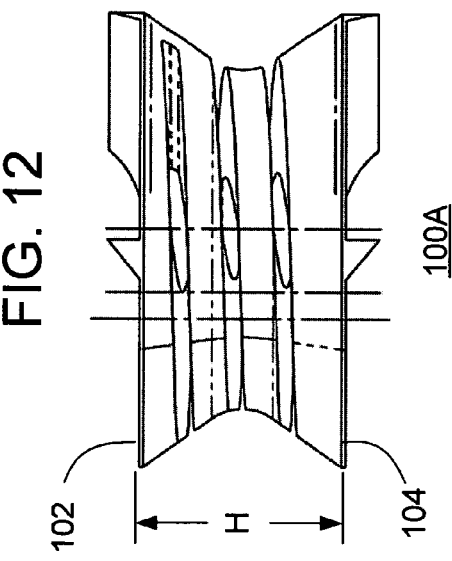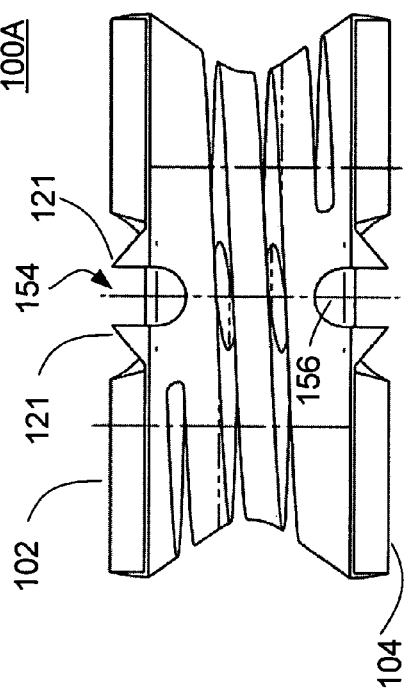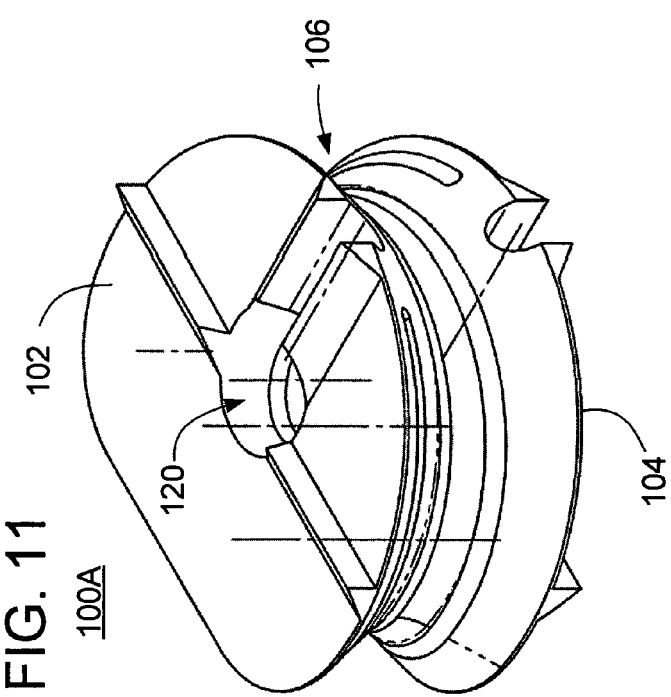

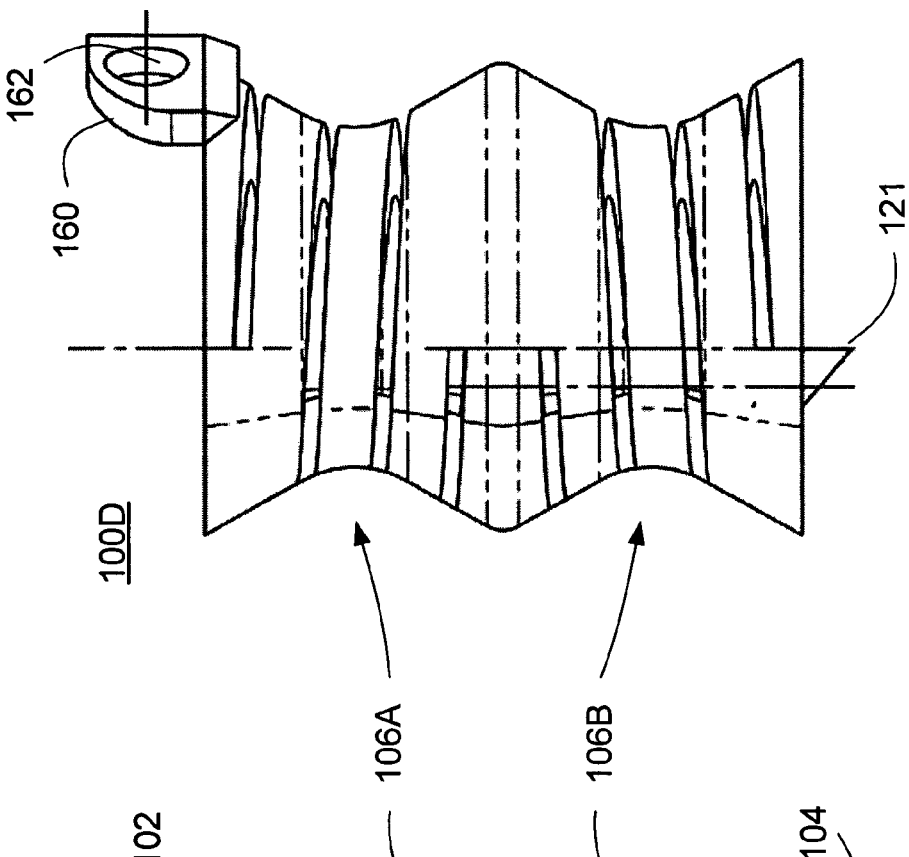
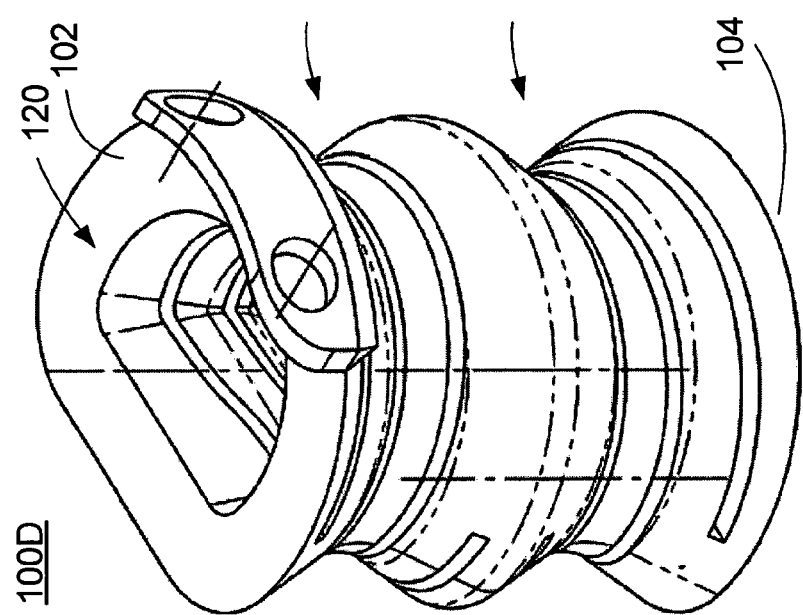

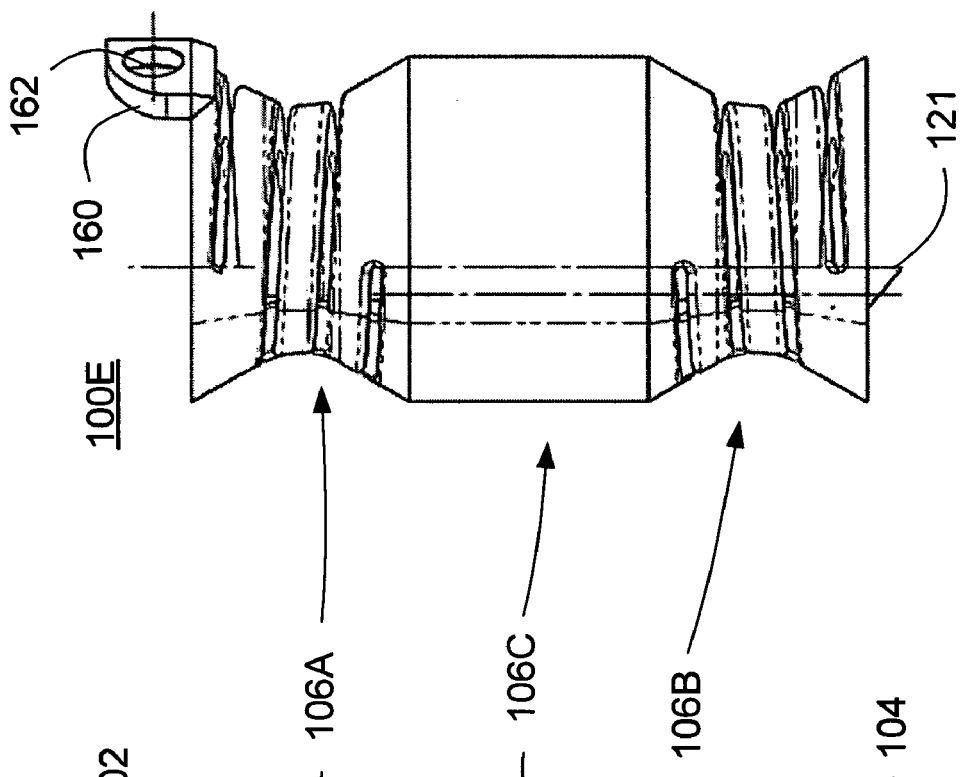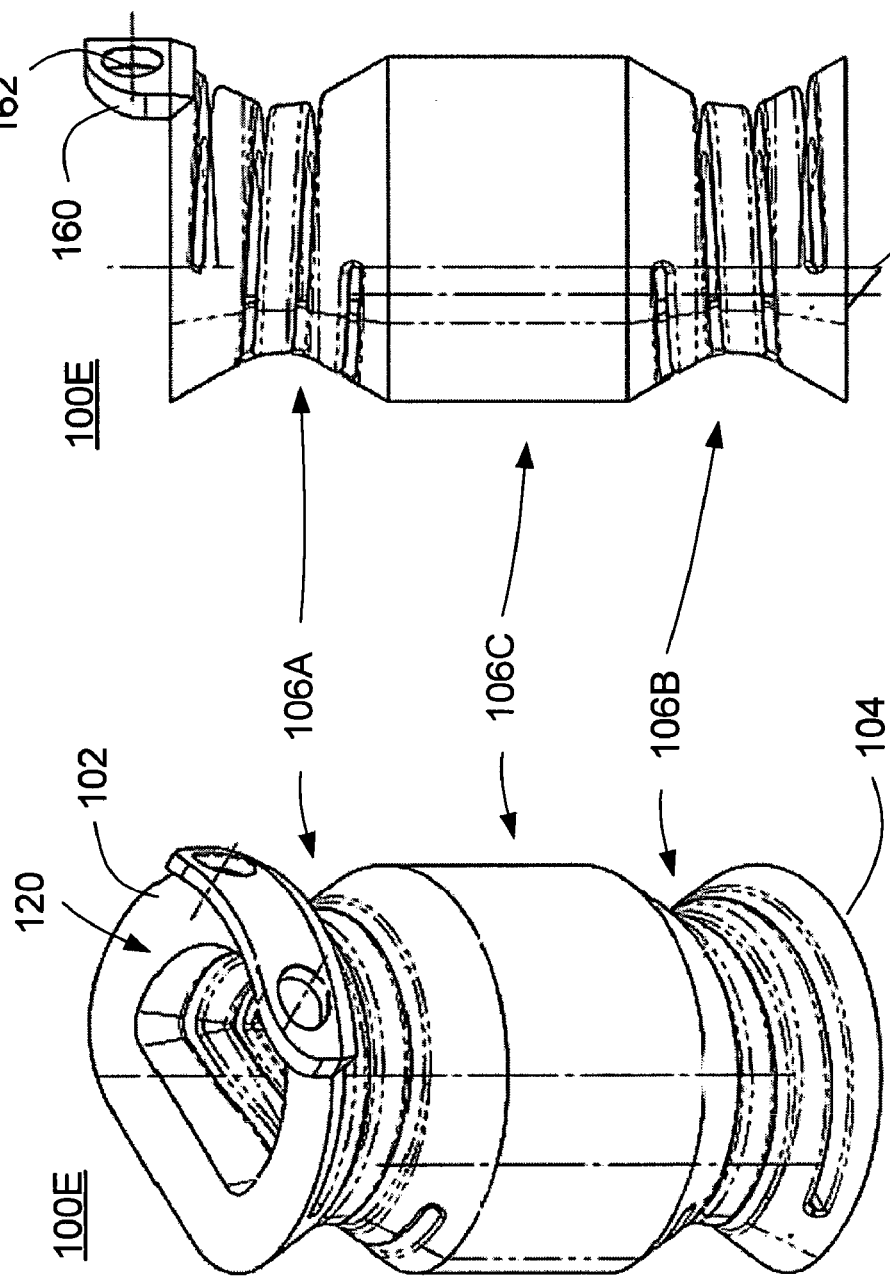

204

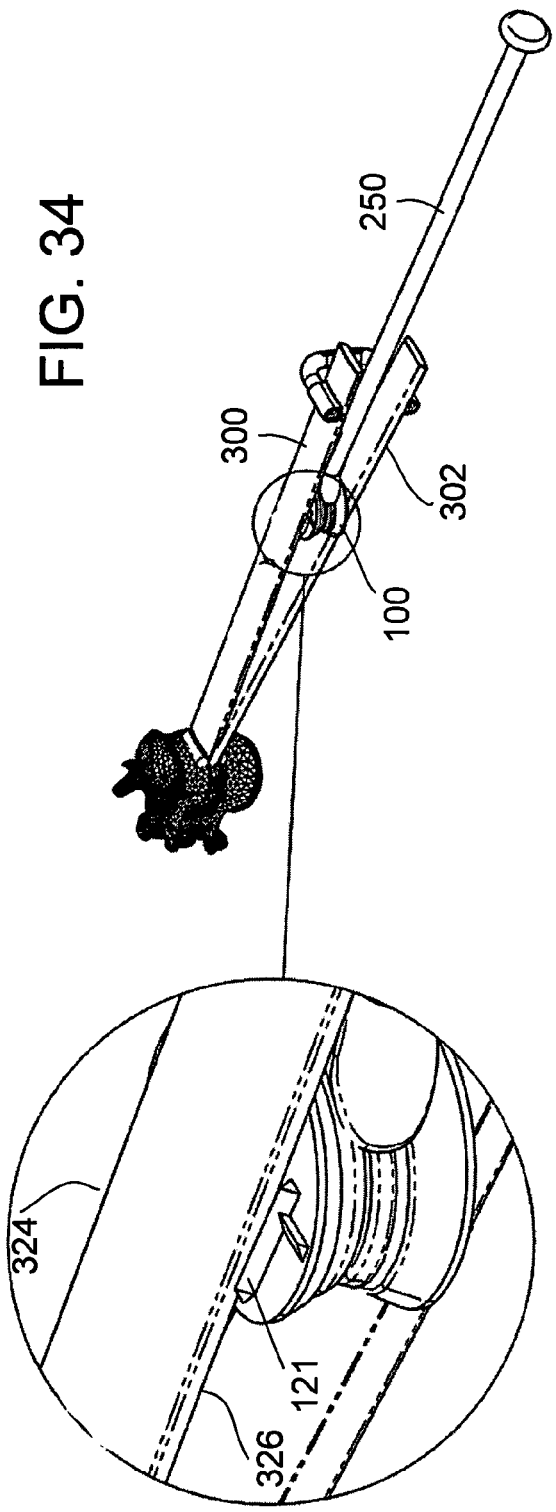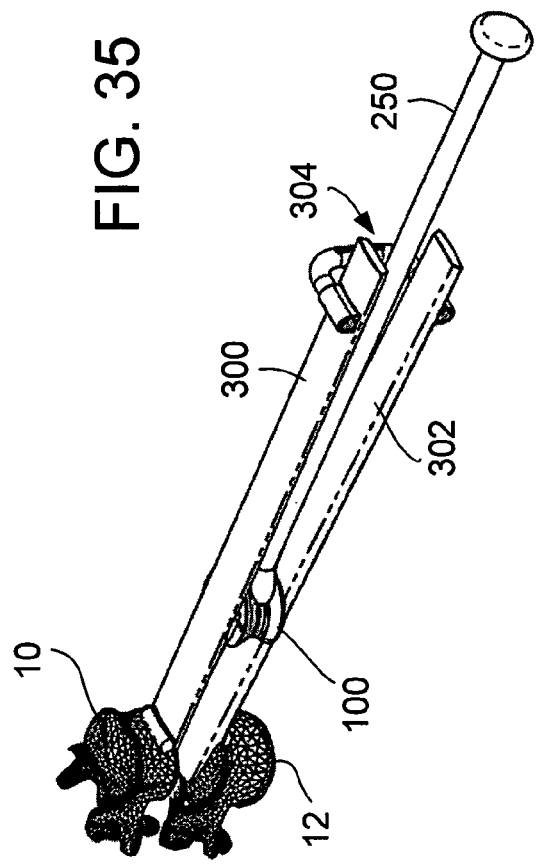

ANTERIOR LUMBAR INTERVERTEBRAL STABILIZER

CROSS REFERENCE TO RELATED APPLICATIONS

This application claims the benefit of U.S. Provisional Patent Application No.: 60/658,345, filed Mar. 3, 2005, the entire disclosure of which is hereby incorporated by reference.

BACKGROUND

The present disclosure generally relates to apparatus and methods for treatment of spinal disorders using an intervertebral prosthesis which is disposed in an intervertebral disc space following removal of a damaged or diseased intervertebral disc.

The objective in intervertebral disc replacement or intervertebral stabilization is to provide a prosthetic disc that combines both stability to support the high loads of the patient's vertebrae and flexibility to provide the patient with sufficient mobility and proper spinal column load distribution.

Numerous artificial intervertebral discs for replacing a part or all of a removed disc have been developed, namely, elastomer discs, ball and socket discs, mechanical spring discs and hybrid discs. Elastomer discs typically include an elastomer cushion which is sandwiched between lower and upper rigid endplates. The elastomer discs are advantageous in that the elastomer cushion functions similar in mechanical behavior to the removed intervertebral disc tissue. However, a disadvantage of this disc type is that the elastomer cushion experiences long term in-vivo problems stemming from microcracking, which detracts from its usefulness as a replacement option. Furthermore, attachment of the flexible elastomer cushion to rigid endplates presents additional difficulties. Examples of elastomer discs are disclosed in U.S. Pat. Nos. 5,702,450; 5,035,716; 4,874,389; and 4,863,477.

Ball and socket discs typically incorporate two plate members having cooperating inner ball and socket portions which permit articulating motion of the members during movement of the spine. The ball and socket arrangement is adept in restoring "motion" of the spine, but, is poor in replicating the natural stiffness of the intervertebral disc. Dislocation and wear are other concerns with this disc type. Examples of ball and socket discs are disclosed in U.S. Pat. Nos. 5,507,816; and 5,258,031.

Mechanical spring discs usually incorporate one or more coiled springs disposed between metal endplates. The coiled springs preferably define a cumulative spring constant sufficient to maintain the spaced arrangement of the adjacent vertebrae and to allow normal movement of the vertebrae during flexion and extension of the spring in any direction. Examples of mechanical spring discs are disclosed in U.S. Pat. Nos. 5,458,642; and 4,309,777.

The hybrid artificial intervertebral disc incorporates two or more principles of any of the aforementioned disc types. For example, one known hybrid disc arrangement includes a ball and socket set surrounded by an elastomer ring. This hybrid disc provides several advantages with respect to load carrying ability, but, is generally complex requiring a number of individual components. Furthermore, long term in vivo difficulties with the elastomer cushion remain a concern as well as wear of the ball and socket arrangement.

Another type of intervertebral disc prosthesis is disclosed in U.S. Pat. No. 5,320,644. With reference to FIGS. 1-3, the '644 patent discloses a unitary intervertebral disc member 1 made from an elastically deformable material. The disc member 1 has parallel slits 5 each arranged at a right angle to the axis of the disc member. The parallel slits 5 partially overlap one another to define overlapping regions 6 between adjacent slits. The overlapping regions 6 create leaf springs 7 for the transmission of forces from one vertebral attachment surface to the other. In regions of adjacent slits 5 where they do not overlap the spring action on the leaf springs 7 is interrupted by fixation zones 9 of solid prosthesis material. The forces acting on the intervertebral disc are transmitted from one leaf spring plane to the next leaf spring plane via the fixation zones 9. The load paths are inherently abrupt with highly localized transfer of load through the sparsely placed fixation zones 9. There are even instances where the entire load is carried through a single fixation zone 9 in the center of the disc. The abrupt load paths can lead to high stress regions, which can detract from the appropriate biomechanical performance, i.e., strength, flexibility, and range-of-motion, of the prosthesis.

U.S. Pat. No. 6,296,664 discloses an intervertebral prosthesis having a disc member defining a longitudinal axis extending the height of the disc member and a lateral axis transverse to the longitudinal axis. The disc member includes an exterior wall which has a slit defined therein. The slit defines a longitudinal component of direction and a lateral component of direction. Preferably, the exterior wall includes a plurality of helical slits, adjacent slits being disposed in at least partial overlapping relation to define an overlapping region. Upon insertion of the disc member within the intervertebral space with the support surfaces in contacting engagement with respective vertebral portions of the adjacent vertebrae, forces exerted by the vertebral portions on the support surfaces are transferred along the exterior wall through the overlapping region.

All of the above intervertebral devices suffer from common problems, for example, they are limited in the reaction forces that they produce in response to compressive forces. For instance, once mechanical spring discs bottom out, there is no further articulation provided. This is undesirable in some applications. Further, the above described devices are not suitable for posterior implantation. Still further the above described devices are difficult to implant, reposition, or remove.

Thus, there has been discovered a need for a new intervertebral stabilizer.

SUMMARY OF THE INVENTION

In accordance with one or more embodiments of the present invention, an intervertebral stabilizer, includes: a first surface operable to engage an endplate of a first vertebral bone of a spine; a second surface spaced apart from the first surface and operable to engage an endplate of an adjacent second vertebral bone of the spine; and a spring element including helical coils disposed between the first and second surfaces and operable to provide reactive forces in response to compression loads from the first and second vertebral bones, wherein at least some diameters of respective turns of the helical coils differ.

Those of the turns having larger diameters are preferably disposed towards the first and second surfaces and those of the turns having smaller diameters are centrally located between the turns having larger diameters. Alternatively or in addition, the cross-sectional profile taken through the spring element is preferably at least partially hourglass shaped. Alternatively, the cross-sectional profile taken through the spring element is a multiple hourglass shape.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

It is noted that the numerous figures herein are drawn substantially to scale at least in terms of the relationships among the elements of the particular views shown.

FIGS. 6-8 illustrate perspective, side (or lateral), and anterior views, respectively, of an intervertebral stabilizer in accordance with one or more further embodiments of the present invention;

FIGS. 11-13 illustrate perspective, side, and anterior views, respectively, of an intervertebral stabilizer in accordance with one or more further embodiments of the present invention;

FIGS. 21-22 illustrate perspective and side views, respectively, of an intervertebral stabilizer in accordance with one or more further embodiments of the present invention;

FIGS. 23-24 illustrate perspective and side views, respectively, of an intervertebral stabilizer in accordance with one or more further embodiments of the present invention;

FIGS. 33-37 are perspective views illustrating an implantation process utilizing the wedge ramps and insertion tools of FIGS. 29-32.

DETAILS OF THE EMBODIMENTS OF THE INVENTION

Figure 1:
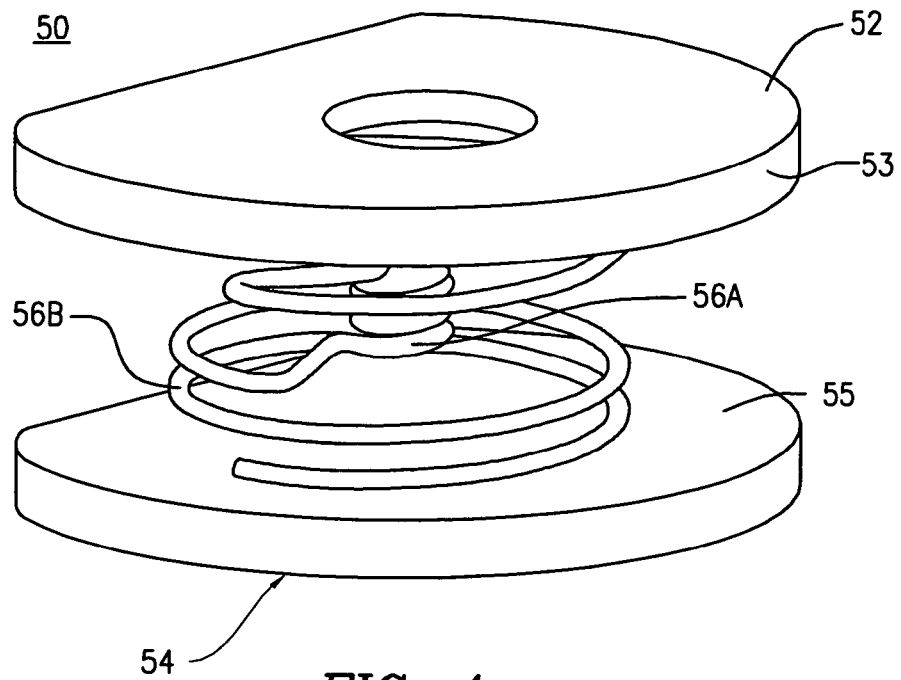
FIGS. 1-2 illustrate perspective and side (or lateral) views, respectively, of an intervertebral stabilizer in accordance with one or more embodiments of the present invention.
Figure 2:
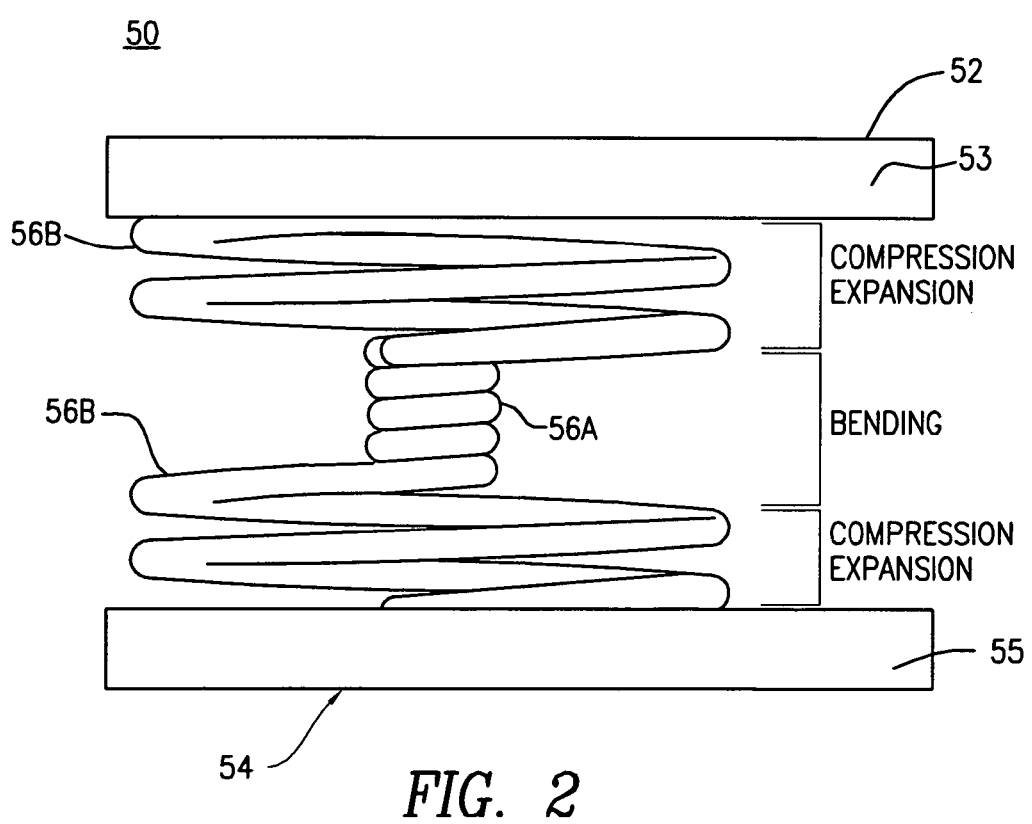

FIGS. 1-2 illustrate an embodiment of a spinal intervertebral stabilizer 50 in accordance with one or more aspects of the present invention. The stabilizer 50 is sized and shaped to fit in the intervertebral space between adjacent vertebral bones of the spine. It is understood that the size and shape of the stabilizer 50 may be adapted to fit in an intervertebral space at any level of the spine, such as the cervical spine, thoracic spine, or lumbar spine. The stabilizer 50 is sized and shaped to be inserted into the inter-vertebral space from an anterior direction. The stabilizer 50 includes an upper surface 52 of a first member 53 and a lower surface 54 of a second member 55 that are operable to engage end plates of the respective vertebral bones. A spring element in the form of a helical coil 56 is interposed between the upper and lower surfaces 52, 54 of the first and second members 53, 55.

The helical coil 56 includes at least one first segment 56A having a first diameter and at least one second segment 56B having a second diameter. In the embodiment shown, two second segments 56B are disposed axially with respect to a single first segment 56A, which is interposed between the second segments 56B. As shown, the stabilizer 50 may provide some movement in compressive and/or expansion directions due to the spaces between the respective turns of the second segments 56B of the helical coil 56. These spaces between the turns may be adjusted to provide differing amounts of compressive or expansion movement of the stabilizer 50. The compressive and expansion movement may also be adjusted by varying material properties of the segments 56B. The stabilizer 50 may also provide some movement in bending due to the first segment 56A of the helical coil 56. More particularly, the first and second segments 56A, 56B of the stabilizer 50 permits movement as to displacement, rotation, subluxation, flexion, extension, bending, or any combination thereof.

Figure 3:
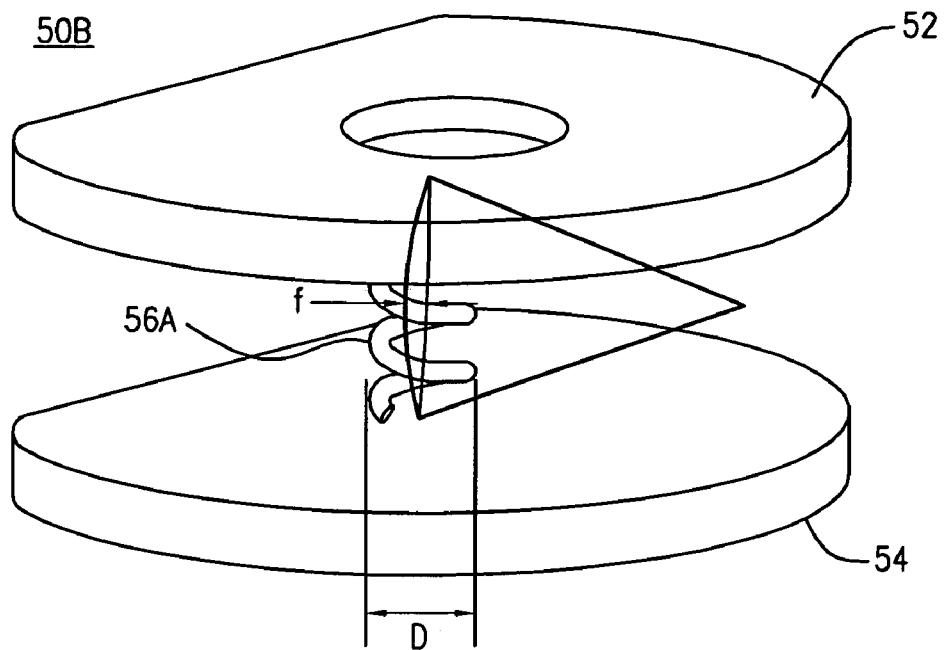
FIGS. 3-4 illustrate perspective views of certain spring features of the intervertebral stabilizer of FIGS. 1-2.
Figure 4:
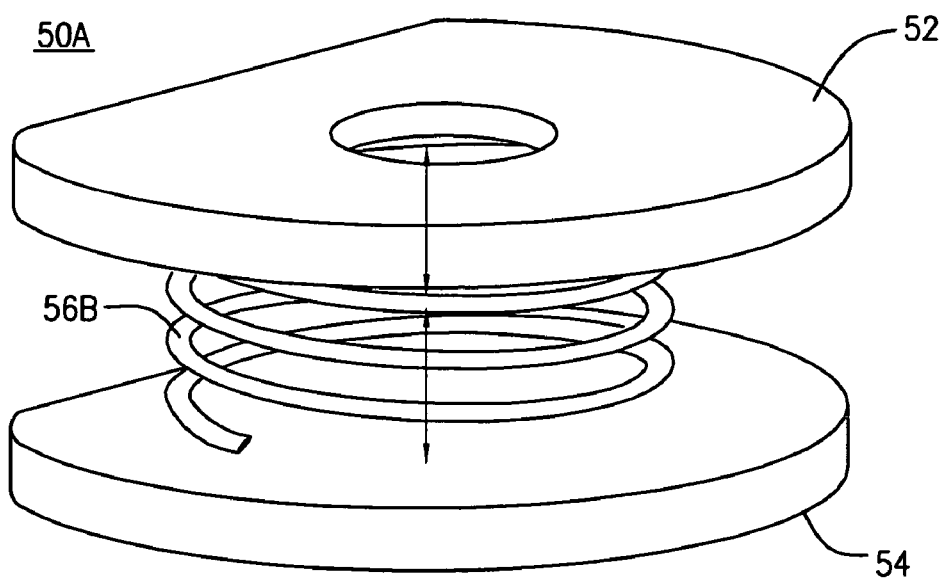

Among the movements permitted by the stabilizer 50 is flexing by collapsing one side of the stabilizer 50 and expanding the other side. The degree of collapsing and expanding of the stabilizer 50 may be varied depending on the spring properties of the first and second segments 56A, 56B of the helical coil 56. In this regard, reference is now made to FIGS. 3-4, which are conceptual illustrations of the spring properties of the first and second segments 56A, 56B, respectively, of the helical coil 56 as if employed separately. As shown in FIG. 3, the relatively small spring diameter of the first segment 56A promotes bending (deflection f) because the deflection f is inversely proportional to an outside diameter D of the turns of the first segment 56A. This may be expressed as follows: $f=k/D$, where k is the spring constant of the spring. Thus, the smaller the diameter D of the first segment 56A, the more deflection f is achieved and vice verse. Notably, the first segment 56A simultaneously prohibits compression and expansion (B) because such movement is directly proportional to the diameter D. This may be expressed as follows: $B=k \cdot D$. In contrast, as the second segment 56B has a relatively larger diameter spring, it promotes compression and expansion, and inhibits bending.

The resultant functionality of the helical coil 56 is that one or more of the segments of the coil 56 permit compression/expansion and inhibit flexion (such as segments 56B), while one or more other of the segments permit flexion and inhibit compression/expansion (such as segment 56A). Thus, the first and second segments 56A, 56B of the stabilizer 50 permit movement as to displacement, rotation, subluxation, flexion, extension, bending, or any combination thereof.

Figure 5:
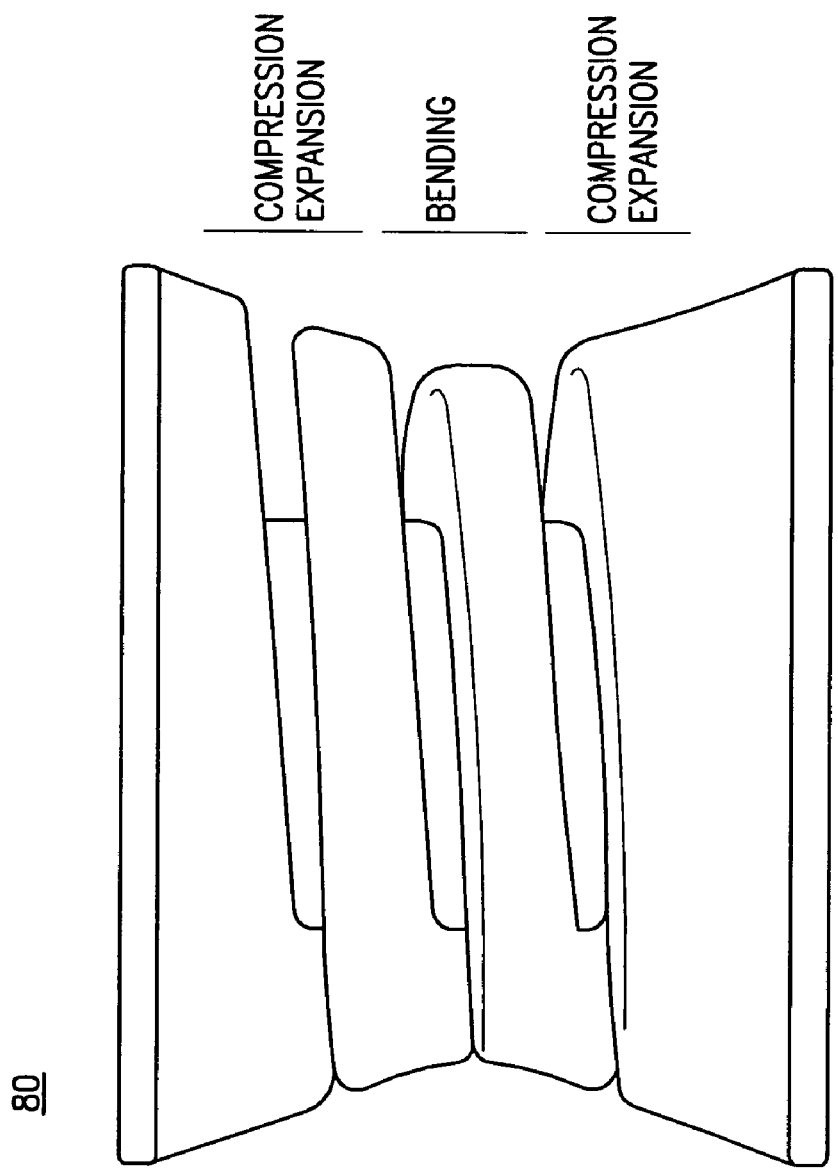
FIG. 5 is a side view of an intervertebral stabilizer in accordance with one or more further embodiments of the present invention.

The functionality of the varying diameter coil segments 56A, 56B may be adapted in an embodiment with a spring element having a more gradually changing diameter as is illustrated in FIG. 5. This embodiment includes a spinal intervertebral stabilizer 80 in accordance with one or more aspects of the present invention. The stabilizer 80 is sized and shaped to fit in the intervertebral space between adjacent vertebral bones of the spine, and as with one or more other embodiments herein, it is understood that the size and shape of the stabilizer 80 may be adapted to fit in an intervertebral space at any level of the spine, such as the cervical spine, thoracic spine, or lumbar spine. As with the stabilizer 50, the stabilizer 80 includes a spring element having a plurality of segments, some of which promote compression/expansion, while others promote flexion. The spring element is in the form of a helical coil of hourglass cross section. These and other properties of the stabilizer 80 will be discussed in more detail herein with reference to several specific examples.

Figure 9:
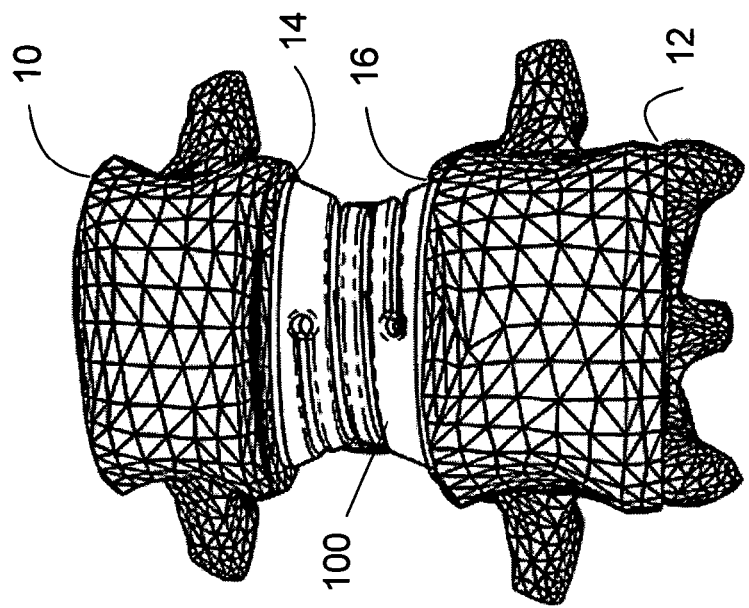
FIGS. 9-10 illustrate perspective and anterior views, respectively, of the intervertebral stabilizer of FIGS. 6-8 in use.
Figure 10:
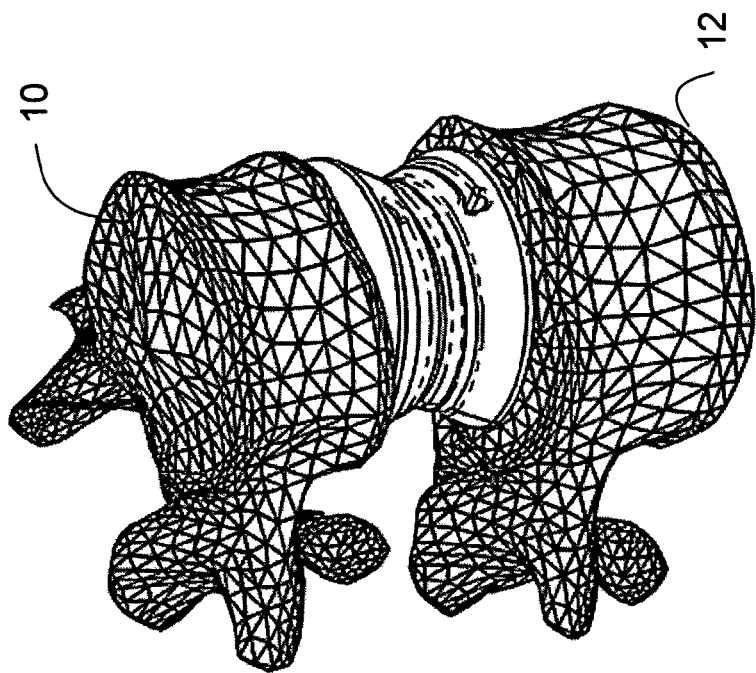

FIGS. 6-8 illustrate an embodiment of a spinal intervertebral stabilizer 100. As best seen in FIGS. 9-10, the stabilizer 100 is sized and shaped to fit in the intervertebral space between adjacent vertebral bones 10, 12 of the spine. It is understood that the size and shape of the stabilizer 100 may be adapted to fit in an intervertebral space at any level of the spine, such as the cervical spine, thoracic spine, or lumbar spine. The stabilizer 100 is sized and shaped to be inserted into the inter-vertebral space from an anterior direction.

The stabilizer 100 includes an upper surface 102 and a lower surface 104 that are operable to engage the end plates 14, 16 of the respective vertebral bones 10, 12. The body 106 of the stabilizer 100 is of generally cylindrical construction. As best seen in FIGS. 7-8, a cross-sectional profile of the body 106 is hourglass shaped. The body 106 also includes a spring element in the form of a helical coil in which a continuous or substantially continuous slot 108 extends helically from a terminal end 108A adjacent the first surface 102 to a terminal end 108B adjacent the second surface 104. The slot 108 provides the stabilizer 100 with a spring capability by creating respective turns or coils of the helical coil. In alternative embodiments, the spring feature of the body 106 may be formed from a helical wound spring, such as of circular, rectangular, or other shape cross-sectional configuration. In a preferred embodiment, the body 106 is formed of a substantially solid cylindrical hollow body in which the helical coils are formed from the substantially continuous slot 108 that is cut into the body 106 through to the hollow portion 120 thereof.

In a preferred embodiment, the upper surface 102, the lower surface 104, and the body 106 are formed as an integral element, e.g., of single-piece construction.

At rest, the stabilizer 100 preferably takes the orientation shown. The spring features of the body 106 are preferably designed such that the stabilizer 100 maintains a minimum distance between the vertebral bones 10, 12 inasmuch as the surfaces 102, 104 may not be compressed towards one another beyond a minimum distance. As shown, the stabilizer 100 provides some movement in the compressive direction because the slot 108 provides some distance between the "coils" of the spring feature. This distance or space between the coils may be adjusted to provide differing amounts of compressive movement of the stabilizer 100. For example, the space may be at a minimum, such as zero, which would inhibit any compressive movement of the stabilizer 100 and also the vertebral bodies.

Although the stabilizer 100 limits the distance between the vertebral bodies, it permits some movement as to displacement, rotation, subluxation, flexion, extension, bending, or any combination thereof. For example, the design permits longitudinal or flexing by collapsing one side of the stabilizer 100 and expanding the other side. Depending on the amount of space provided between the coils of the spring feature of the body 106, the center of rotation associated with flexing may be well outside the inter-vertebral space, potentially one to five inches or more outside the inter-vertebral space.

As best seen in FIG. 7, the upper surface 102 includes a peripheral edge 112 that overhangs at least one coil of the body 106, and preferably overhangs all of the coils of the body 106. Similarly, the lower surface 104 includes a peripheral edge 114 that overhangs at least one coil of the body 106, and preferably all of the coils of the body 106. In this regard, a moment arm Ma is defined by a lateral distance between an outer surface of the at least one coil 110 of the body 106 and the peripheral edge 112 of the upper surface 102. The same or another moment arm may also be defined in terms of the peripheral edge 114 of the lower surface 104 and the outer surface of the coil 110. Those skilled in the art will appreciate that the moment arm Ma may also be defined in terms of the point at which the slot 108 collapses and respective adjacent coils engage one another. Irrespective of how the moment arm is defined, a compressive force Fc acting on, for example, at least a portion of the peripheral edge 112 and any portion of the lower surface 104 tends to collapse the spring of the body 106 and full compression of the spring results in closure of the slot 108 in the vicinity of the force Fc such that adjacent coils engage one another. Further compressive force Fc will work in conjunction with the moment arm Ma such that portions of the coils on an opposite side of the spring of the body 106 from the engaged coils tends to expand.

A surgeon is preferably provided with a plurality of different sized intervertebral stabilizers 100 that he or she may utilize to fit the particular physiology of the patient. In general, relatively larger intervertebral stabilizers 100 will be useful in the lumbar region of the spine, smaller sized intervertebral stabilizers 100 will be useful in the thoracic region of the spine, and still smaller sized intervertebral stabilizers 100 will be useful in the cervical spine. By way of example, it is preferred that a height H of the intervertebral stabilizer 100 (e.g., measured between the upper and lower surface 102, 104) is between about 8.0 mm to about 18.0 mm for use in the lumbar region of the spine. More particularly, a number of different sized intervertebral stabilizers 100 are preferably available to the surgeon, such as having a height of between (i) about 8.0 mm to 10.0 mm; (ii) about 10.0 mm to about 14.0 mm; and (iii) about 14.0 mm to about 18.0 mm.

The spring feature of the body 106 is preferably formed utilizing about 1.0 slot or 2.0 coils when the height of the intervertebral stabilizer 100 is about 8.0 mm to about 10.0 mm. In this context, about two turns or coils are created by one slot traversing at least partially around the body 106. The spring feature of the body 106 is preferably formed from about 2.0 slots or 3.0 coils when the height of the intervertebral stabilizer 100 is about 10.0 mm to about 14.0 mm. Additionally, the spring feature of the body 106 is preferably formed from about 3.0 slots or 4.0 coils when the height of the intervertebral stabilizer 100 is about 14.0 mm to about 18.0 mm.

With reference to FIGS. 11, 12, and 13, perspective, side, and anterior views, respectively, of an intervertebral stabilizer 100A are illustrated. The intervertebral stabilizer 100A is preferably used in the cervical spine. In this regard, the height of the intervertebral stabilizer 100A is preferably between about 6.0 mm to about 9.0 mm. The surgeon is preferably provided with a plurality of different sized intervertebral stabilizers 100A for the cervical region of the spine. In particular, an intervertebral stabilizer 100A having a height of about 5.0 mm to about 7.0 mm is formed in which the spring feature of the body 106 is formed utilizing about 3.0 slots or 4.0 coils. In a further embodiment of the intervertebral stabilizer 100A, the height is about 7.0 mm to about 9.0 mm and the spring feature of the body 106 is formed from about 4.0 slots or 5.0 coils.

As best seen in FIGS. 6 and 11, the intervertebral stabilizers 100, 100A may include one or more bone adhesion facilitating elements 121 operable to promote bone adhesion to at least one of the upper and lower surface 102, 104. As shown, the bone adhesion facilitating elements 121 may include one or more spikes oriented in any number of directions and being of generally triangular cross-section. Other embodiments of the invention contemplate that the bone adhesion facilitating elements are formed from one or more keels extending from the upper and/or lower surface 102, 104; and/or from one or more roughening elements (such as dimpling or knurling) on one or both of the upper and lower surfaces 102, 104.

Figure 14:
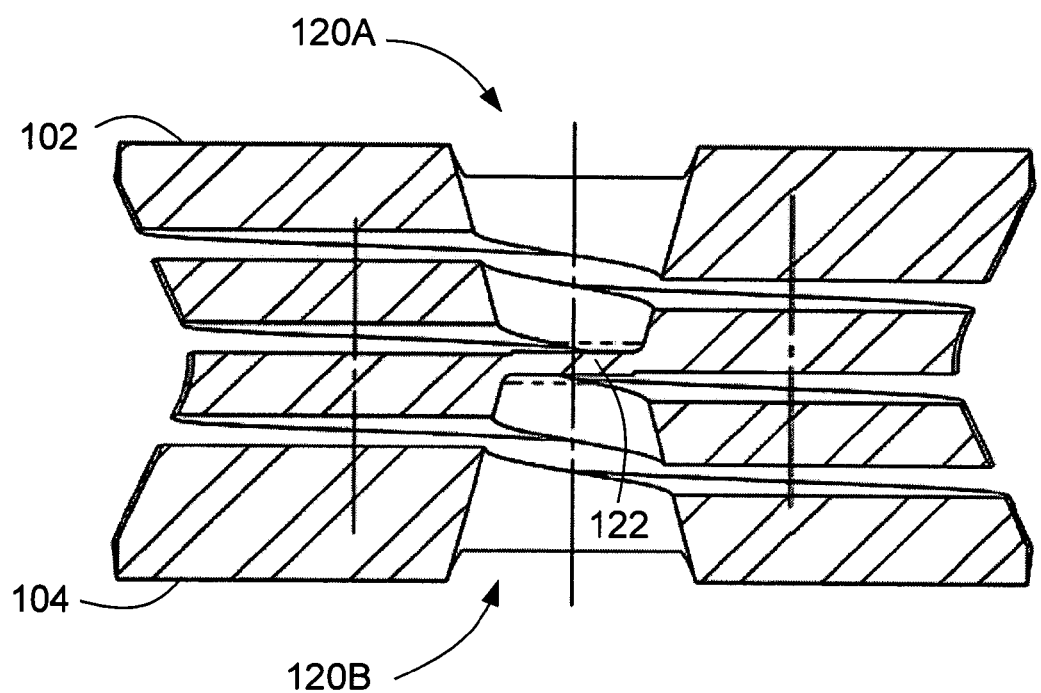
FIG. 14 is a sectional view of an intervertebral stabilizer in accordance with one or more further embodiments of the present invention.

In one or more embodiments, the hollow portion 120 of the body 106 may extend from the upper surface 102 to the lower surface 104 unimpeded. With reference to FIG. 14, in one or more further embodiments, the hollow portion 120 may include a membrane 122 disposed in the passage and substantially closing off the passage to inhibit bone growth therethrough. Preferably, the membrane 122 is formed as an integral element of the body 106. For example, the hollow portion 120 may be formed from first and second hollow portions 120A, 120B that do not pass all the way through the body 106. With or without the membrane 122, the hollow portion 120 is preferably of hourglass shape.

As best seen in FIG. 14, with or without the membrane 122, the shape of the hollow portion 120 is preferably also hourglass shaped. Although the present invention is not limited to any particular theory of operation, it is believed that such an hourglass shaped hole or hollow portion 120 maximizes or at least significantly increases the moment arm Ma, the offset between the compressive load application point at the peripheral edge (e.g. at 112A in FIG. 1) and the outer surface of the spring element (e.g., at 110).

Figure 16:
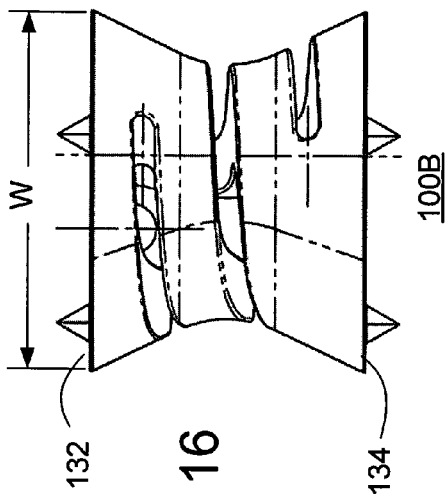
FIGS. 15-17 illustrate perspective, anterior, and side views, respectively, of an intervertebral stabilizer element in accordance with one or more further embodiments of the present invention.
Figure 17:
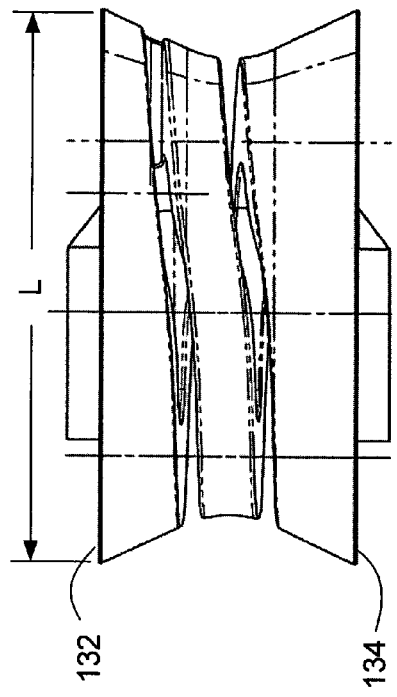
Figure 15:
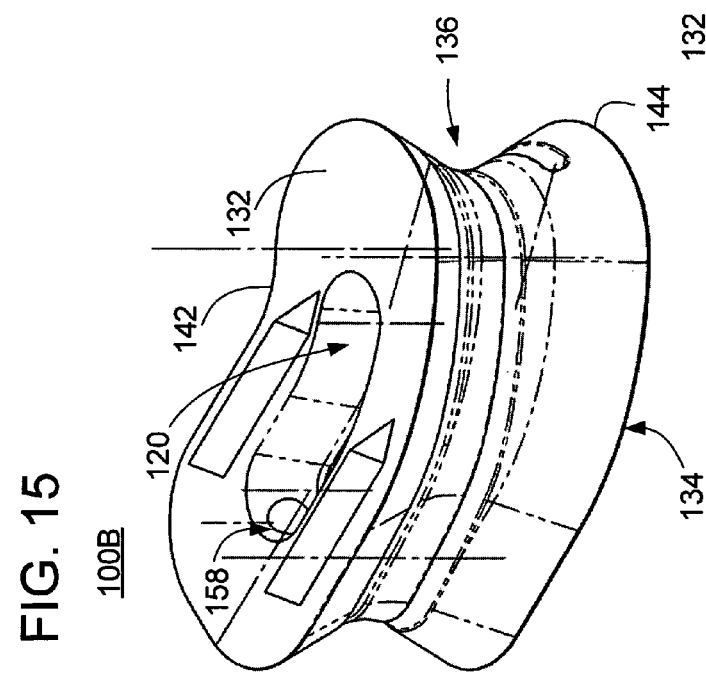

Reference is now made to FIGS. 15-17, which illustrate perspective, anterior, and side views, respectively, of an alternative embodiment of a spinal inter-vertebral stabilizer element 100B. The stabilizer element 100B may include some or all of the features discussed hereinabove with respect to the stabilizers 100 and/or 100A. Respective peripheral edges 142 and 144 of the upper and lower surfaces 132, 134 circumscribe a kidney shape. In use, two of the stabilizer elements 100B (mirror images of one another) are inserted into a single intervertebral space such that an overall envelope created by at least portions of the peripheral edges 142 and/or 144 of the two stabilizer element 100B approximate the shape of the intervertebral space.

The intervertebral stabilizer 100B is preferably sized and shaped to be inserted posteriorly or transversely into the intervertebral space. In this regard, the stabilizer element 100B preferably includes a length L measured along an anterior-to-posterior direction of the spine and a width W along a lateral direction of the spine. The width of the stabilizer element 100B is preferably smaller than the length thereof such that the stabilizer 100B may be implanted from the posterior or transverse-posterior direction into the intervertebral space.

As with the intervertebral stabilizer 100 of FIGS. 6-8, the intervertebral stabilizer element 100B is preferably provided to the surgeon in a number of different sizes (for each mirror image thereof) to accommodate different levels in the spine and/or different physiology of a given patient. It is preferred that the height H of the stabilizer element 100B (e.g., measured between the upper and lower surface 132, 134) adheres to the various dimensions discussed hereinabove with respect to the stabilizer 100. Further, the height of the stabilizer element 100B is preferably characterized as being one of: (i) about 7.0 mm to about 15.0 mm when the spring element of the body 136 includes about 1.0 slot or 2.0 coils; (ii) about 11.0 mm to about 20.0 mm when the spring element of the body 136 includes about 2.0 slots or 3.0 coils; and (iii) about 13.0 mm to about 26.0 mm when the spring element of the body 136 includes about 3.0 slots or 4.0 coils.

Figure 19:
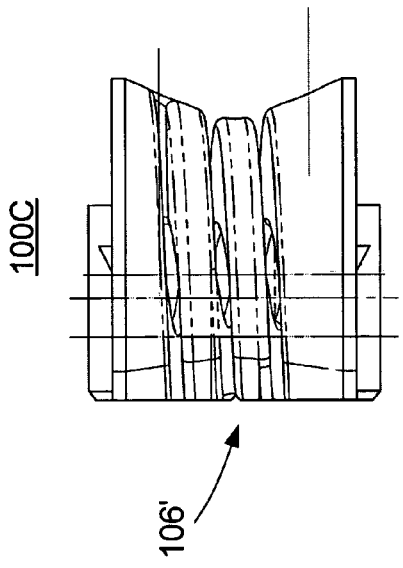
FIGS. 18-20 illustrate perspective, side, and cross-sectional views, respectively, of an intervertebral stabilizer in accordance with one or more further embodiments of the present invention.
Figure 20:
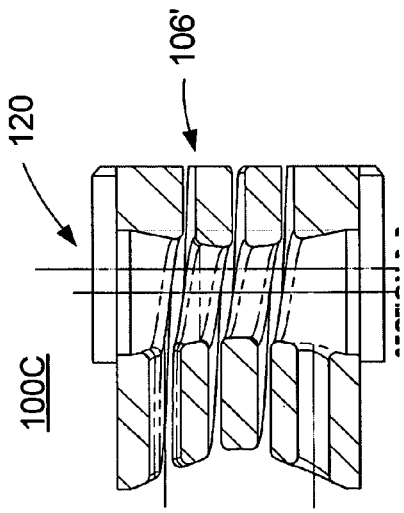
Figure 18:
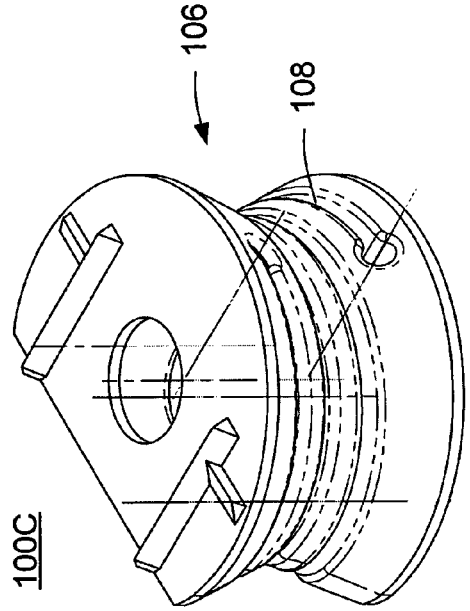

Reference is now made to FIGS. 18-20, which are perspective, side and cross-sectional views, respectively, of a further embodiment 100C of the present invention. In many ways, the stabilizer 100C is substantially the same as the stabilizer 100 of FIGS. 6-8. Indeed, the stabilizer 100C includes an upper surface 102 and a lower surface 104 that are operable to engage the end plates 14, 16 of the respective vertebral bones 10, 12. The body 106 of the stabilizer 100C is of generally cylindrical construction and includes a spring element in the form of a helical coil in which a continuous or substantially continuous slot 108 extends helically from a terminal end adjacent the first surface 102 to a terminal end adjacent the second surface 104. Unlike the prior embodiments, the cross-sectional profile of the body 106 is only partially hourglass shaped. Indeed, the body 106 includes a substantially flat portion 106' that does not have an hourglass contour. The detailed discussion above regarding the full hourglass-shaped body 106 applies with equal weight here, although those skilled in the art will appreciate that the principles of operation of the full hourglass-shaped body 106 may also be inherently extended. A hollow portion or aperture 120 preferably extends from the surface 102 to the surface 104. The hollow portion 102 may also include the membrane 122 (FIG. 14), and/or may also be hourglass shaped.

Reference is now made to FIGS. 21-22, which are perspective and side views, respectively, of a further embodiment of the present invention. The stabilizer 100D includes an upper surface 102 and a lower surface 104 that are operable to engage the end plates of respective vertebral bones. The body 106 of the stabilizer 100D includes a plurality of hourglass shaped segments 106A, 106B, etc. (two such segments being shown for illustration). As with some of the prior embodiments, the cross-sectional profile of the body 106 is hourglass shaped; however, this embodiment of the invention include multiple hourglass shapes in axial alignment. A hollow portion or aperture 120 preferably extends from the surface 102 to the surface 104. The hollow portion 102 may also include the membrane 122 (FIG. 14), and/or may also be hourglass shaped. The detailed discussion above regarding a single hourglass-shaped body 106 applies with equal weight here, although those skilled in the art will appreciate that the principles of operation of the single hourglass-shaped body 106 may also be inherently extended.

As best seen in FIG. 22, the intervertebral stabilizer 100D may include one or more bone adhesion facilitating elements 121 operable to promote bone adhesion to at least one of the upper and lower surface 102, 104. The bone adhesion facilitating elements 121 may include one or more spikes oriented in any number of directions and being of generally triangular cross-section. Other embodiments of the invention contemplate that the bone adhesion facilitating elements are formed from one or more keels extending from the upper and/or lower surface 102, 104; and/or from one or more roughening elements (such as dimpling or knurling) on one or both of the upper and lower surfaces 102, 104. Alternatively or in addition, the stabilizer 100D may include a flange 160 of generally transverse orientation with respect to the end surface (e.g., surface 102) and operable to engage a sidewall of the vertebral bone by driving one or more screws through aperture(s) 162 of the flange 160 into the vertebral bone. As shown, the stabilizer 100D includes one or more bone adhesion facilitating elements 121 (e.g., spikes) on the surface 104 and a flange 160 extending from the surface 102. Other combinations may be employed without departing from the spirit and scope of the invention.

Reference is now made to FIGS. 23-24, which are perspective and side views, respectively, of a further embodiment of the present invention. While the embodiments of the invention discussed above may be used to stabilize a single pair of vertebral bones, the stabilizer 100E is operable to accommodate a larger space for multiple levels of intervertebral bones. The stabilizer 100E includes an upper surface 102 and a lower surface 104 that are operable to engage the end plates of respective vertebral bones. The vertebral bones, however, need not be adjacent to one another; rather, a vertebral bone of an intervening level may be removed and the remaining vertebral bones may be stabilized using the stabilizer 100E. The body 106 of the stabilizer 100E includes a plurality of axially aligned, hourglass shaped segments 106A, 106B (two such segments being shown for illustration). A further segment 106C is interposed between the hourglass segments 106A, 106B, where the segment 106C does not include a spring feature. The segment 106C accounts for the removed vertebral bone. As shown, the stabilizer 100E includes one or more bone adhesion facilitating elements 121 (e.g., spikes) on the surface 104 and a flange 160 extending from the surface 102. Other combinations may be employed without departing from the spirit and scope of the invention.

Figure 25:
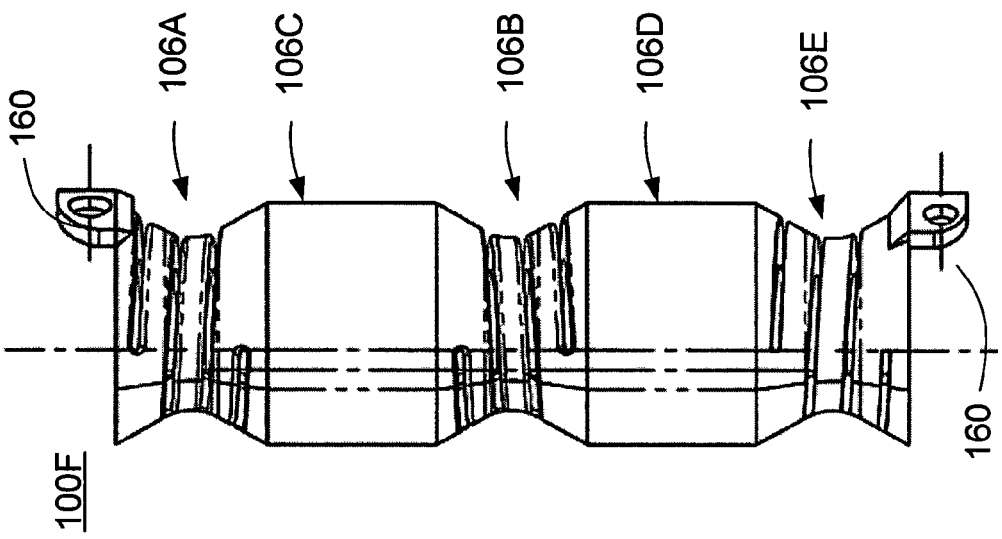
FIGS. 25-26 illustrate perspective and side views, respectively, of an intervertebral stabilizer in accordance with one or more further embodiments of the present invention.
Figure 26:
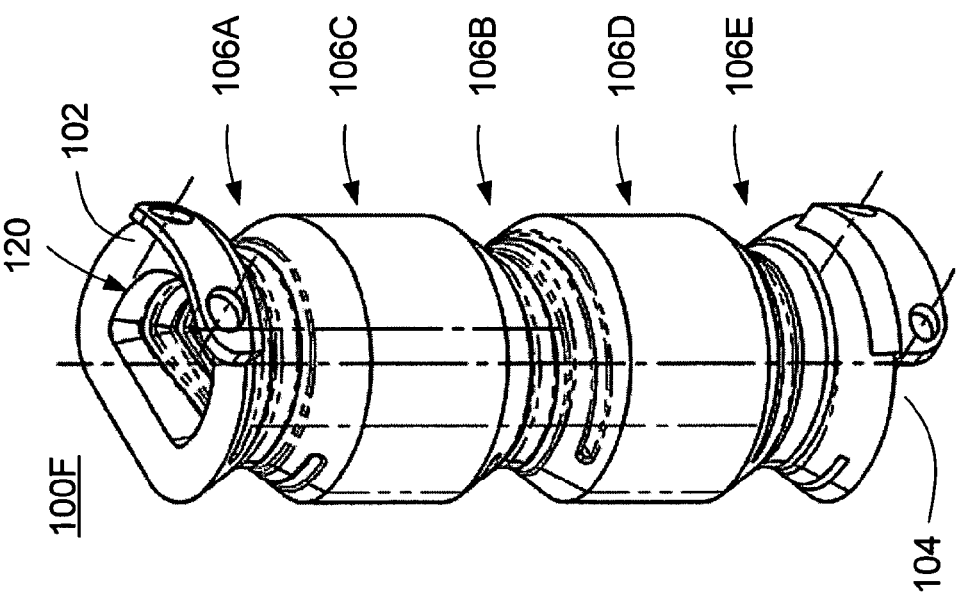

Reference is now made to FIGS. 25-26, which are perspective and side views, respectively, of a further embodiment 100F of the present invention. As with the stabilizer 100E of FIGS. 23-24, the stabilizer 100F is operable to accommodate multi-level stabilization. The stabilizer 100F includes an upper surface 102 and a lower surface 104 that are operable to engage the end plates of respective vertebral bones. Again, the vertebral bones are not adjacent to one another; rather, two or more vertebral bones of intervening level(s) may be removed and the remaining vertebral bones may be stabilized using the stabilizer 100F. The body 106 of the stabilizer 100F includes a plurality of axially aligned, hourglass shaped segments 106A, 106B, 106E (three such segments being shown for illustration). Further segments 106C and 106D are interposed between the hourglass segments 106A, 106B and between 106B, 106E, respectively. The segments 106C and 106D do not include spring features as they account for the removed vertebral bones. As shown, the stabilizer 100E includes a flange 160 on the surfaces 102, 104 to secure the stabilizer 100F. It is noted that further bone adhesion promoting elements may also be employed without departing from the spirit and scope of the invention.

Figure 27:
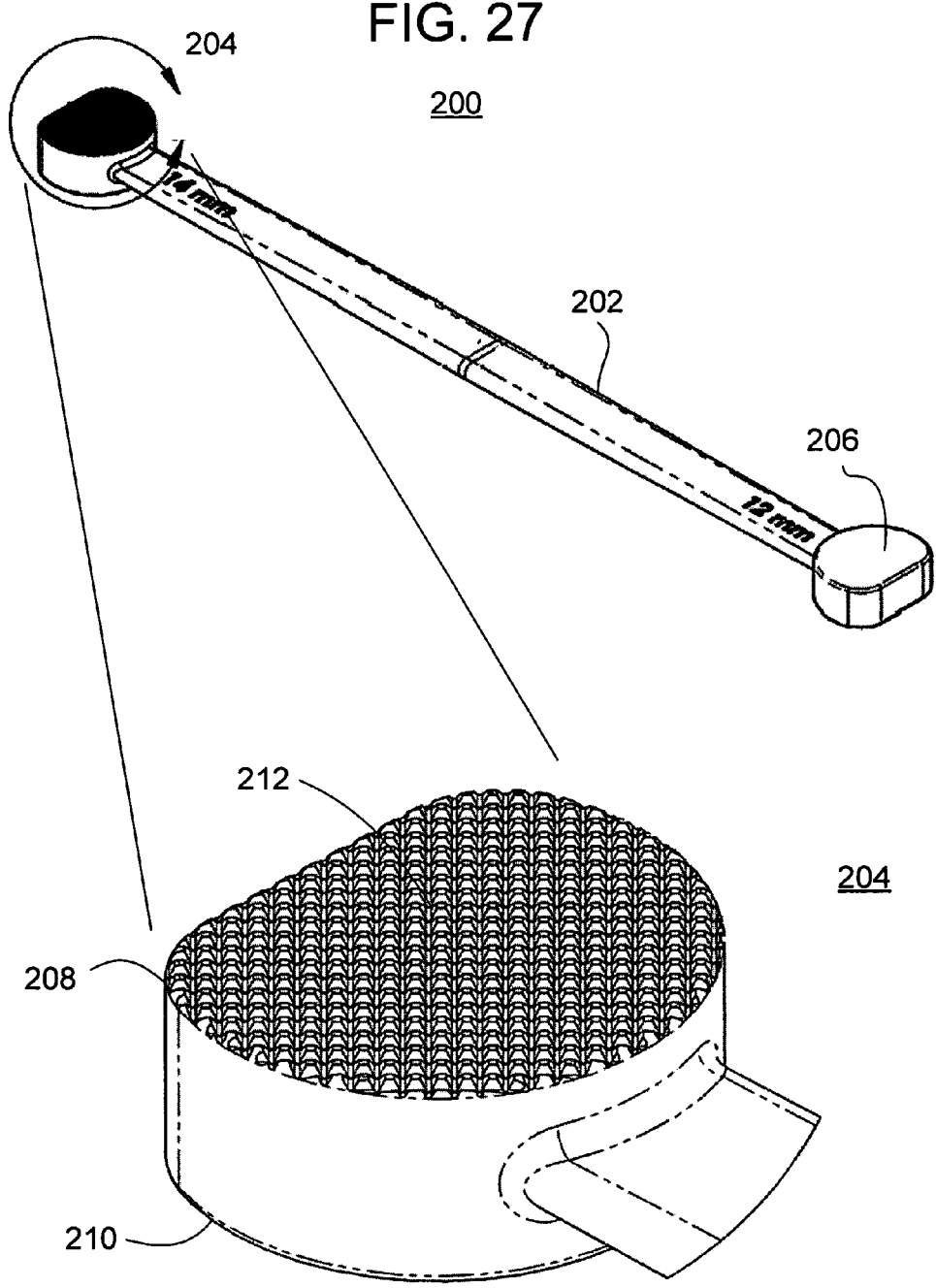
FIG. 27 is a perspective view of an intervertebral trial in accordance with one or more embodiments of the present invention.

Reference is now made to FIGS. 27-39, which illustrate various instrumentations for implanting, for example, the intervertebral stabilizer 100 into a patient. FIG. 27 is a perspective view of an intervertebral trial 200 which is preferably used to prepare the end plates 14, 16 of the intervertebral bones 10, 12, respectively, prior to implantation of the stabilizer 100. More particularly, after anterior incision and access to the intervertebral bones 10, 12 is obtained, the intervertebral space between the end plates 14, 16 is evacuated by removing the disk, some connecting tissue, etc. Next, the trial 200 is utilized to abrade the end plates 14, 16 of the vertebral bones 10, 12. The trial 200 includes a handle 202 and at least one spacer element 204. In a preferred embodiment, another spacer 206 (preferably of different size or character) is included at an opposite end of the handle from the spacer 204. For purposes of brevity, reference will now be made only to spacer element 204, it being understood that the description of spacer 204 may be applied to spacer 206 with equal force.

The spacer element 204 depends from the handle 202 and is preferably sized and shaped to fit in the intervertebral space between the respective end plates 14, 16. The spacer element 204 includes an upper surface 208 and a lower surface 210 that are spaced apart by a height dimension. Preferably, the height is of a sufficient magnitude to at least slightly expand the intervertebral space when the spacer element 204 is urged between the end plates 14, 16. More particularly, the upper surface 208 preferably engages the end plate 14, while the lower surface 210 engages the end plate 16.

At least one of the upper and lower surfaces 208, 210 preferably includes a roughening element 212, such that insertion of the spacer element 204 into the intervertebral space abrades the associated end plate in preparation for implantation of the intervertebral stabilizer 100. In a preferred embodiment, both the upper and lower surface 208, 210 include a roughening element 212 such that insertion of the spacer element 204 into the intervertebral space simultaneously abrades both end plates 14, 16. Preferably, the roughening element is formed from substantially sharp knurling disposed on the respective surfaces 208, 210.

Figure 28:
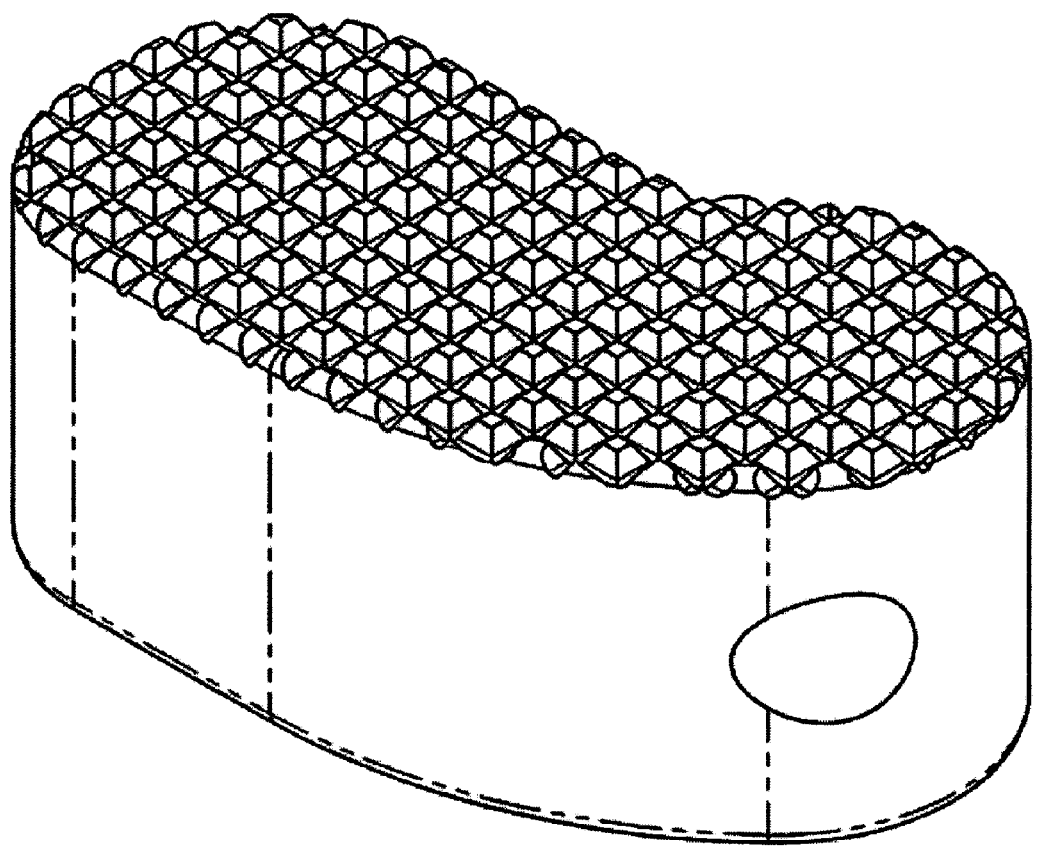
FIG. 28 is a perspective view of an alternative configuration of a spacer for the intervertebral trial of FIG. 27.

With reference to FIG. 28 the shape of the spacer element 204 may be kidney shaped for posterior or lateral implantation.

In a preferred embodiment, the surgeon is provided with a plurality of trials 200, each with differing sized spacer elements 204, 206, such that the surgeon may choose an appropriate sized trial 200 in order to prepare the intervertebral space for implantation. In addition, the plurality of trials 200 may include differing levels of roughness, for example, by adjusting the sharpness and magnitude of the knurling 212. The abrasion of the end plates 14, 16 facilitates bone growth and secure engagement of the upper and lower surfaces 102, 104 of the stabilizer 100 upon implantation into the intervertebral space.

Figure 29:
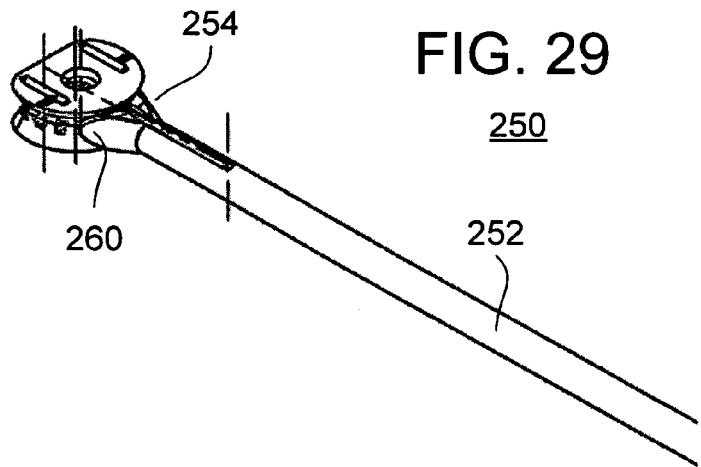
FIGS. 29-31 illustrate perspective, top, and lateral cross-sectional views, respectively, of an insertion tool suitable for implanting one or more of the intervertebral stabilizers herein.
Figure 30:
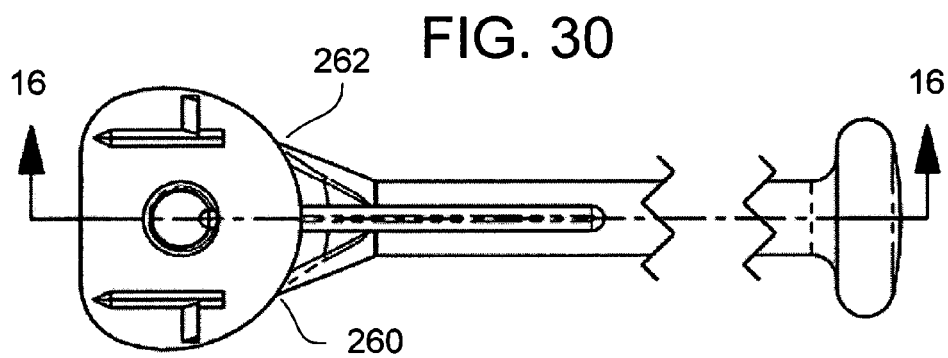
Figure 31:
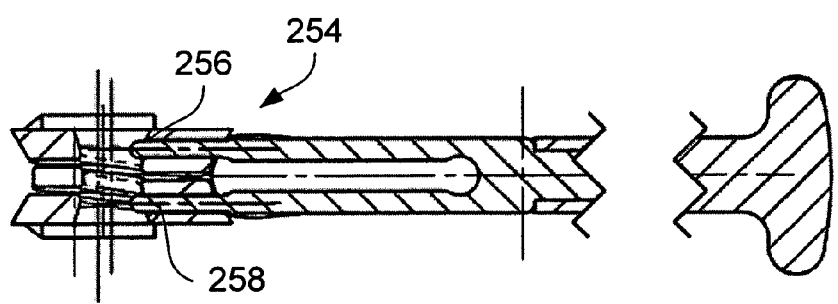

With reference to FIGS. 29, 30 and 31, an insertion tool 250 is preferably utilized to implant an intervertebral stabilizer, such as one or more of the intervertebral stabilizers discussed above into the intervertebral space. For purposes of discussion, reference to the stabilizer 100 of FIGS. 6-8 will be made, it being understood that the description may be applied to the other stabilizer embodiments contemplated herein.

The insertion tool 250 includes a handle 252 and a head 254. The head 254 is operable to releasably engage the intervertebral stabilizer 100 such that the surgeon may manipulate the position of the stabilizer 100 by way of the handle 252 in order to urge the stabilizer 100 into the intervertebral space. As best seen in FIG. 31, the head 254 includes at least a pair of spaced apart pins 256, 258 that facilitate the engagement between the head 254 and the intervertebral stabilizer 100.

As best seen in FIGS. 6 and 8, the intervertebral stabilizer 100 (or any of the other embodiments herein) may include at least a pair of spaced apart apertures 150, 152 operable to receive the pins 256, 258 of the insertion tool 250. As shown, a longitudinal axis A of the stabilizer 100 is normal to the first and second surface 102, 104 and the apertures 150, 152 extend transversely with respect to the longitudinal axis A. The apertures 150, 152 may extend at least partially into the body 106, although it is preferred that the apertures 150, 152 extend all the way through the body 106 into the hollow portion 120. As the stabilizer 100 is intended for anterior implantation, the apertures 150, 152 are preferably disposed on an anteriorly directed side of the body 106. Thus, as best seen in FIGS. 29 and 30, the insertion tool 250 engages the intervertebral stabilizer 100 from the anterior direction such that the surgeon may urge the stabilizer 100 into the intervertebral space from the anterior direction.

Further, the apertures 150, 152 are preferably positioned longitudinal with respect to one another, parallel to the longitudinal axis A. For example, the aperture 150 is disposed toward the first surface 102 and the second aperture 152 is disposed toward the second surface 104. As shown in FIG. 8, the apertures 150, 152 are entirely within the body 106 such that they form a closed interior surface. In a preferred embodiment, the apertures 150, 152 are disposed at terminal ends 108A, 108B of the slit 108 such that the slit 108 communicates with the interior of the respective apertures 150, 152.

As shown in FIGS. 11 and 13, an alternative embodiment may provide a pair of apertures 154, 156 that extend only partially into the body 106 such that respective slots are formed at the first and second surfaces 102, 104. In a preferred embodiment, one or more spikes, keels, or roughening elements 121 are disposed at least partially along the slot. For example, when a pair of spikes 121 are provided along the slot, a dual function may be enjoyed, namely: (i) the spikes assist in forming the slot, thereby facilitating engagement between the insertion tool 250 and stabilizer 100A; and (ii) once implanted, the stabilizer 100A is encouraged to remain in the implanted position owing to the spikes 121 engaging the respective end plates 14, 16.

As best seen in FIGS. 15 and 16, one or more apertures 158 (one aperture being shown for simplicity) may be provided in the body 136 of the stabilizer element 100B in order to assist in the implantation of the element 100B into the intervertebral space from a posterior or transverse posterior direction. Thus, the aperture 158 is posteriorly directed.

Turning again to FIGS. 29-31, the pins 256, 258 are preferably flexible in a direction parallel to the longitudinal axis A (FIG. 6) of the stabilizer 100. Thus, assuming that the pins are spaced apart at an appropriate distance, the apertures 150, 152 urge the pins 254, 258 apart when the head 254 engages the stabilizer 100. Similarly, depending on the spring constant of the spring feature of the stabilizer 100 as compared with the flexibility of the pins 254, 258, the pins 254, 258 may urge the upper and lower surface 102, 104 together when the head 254 engages the stabilizer 100.

As best seen in FIG. 31, a height of the head 254 (measured parallel to the longitudinal axis A) is preferably less than the height of the stabilizer 100. This insures that the head 254 does not interfere with the implantation of the stabilizer 100 in the intervertebral space. As the cross-sectional profile of the body 106 is hourglass shaped, the head 254 is preferably sized such that it at least partially enters into the depression defined by the hourglass shape of the body 106. It is preferred that the contour of the head 254 matches the curvature of the body 106 as is best seen in FIG. 31. Further, the head 254 preferably flairs out in a transverse (e.g., perpendicular) direction to the longitudinal axis A and terminates at respective prongs 260, 262 that provide lateral engagement with the body 106 of the stabilizer 100. This advantageously assists in the lateral stability of the engaged insertion tool and stabilizer 100 as the stabilizer 100 is implanted into the intervertebral space.

Figure 32:
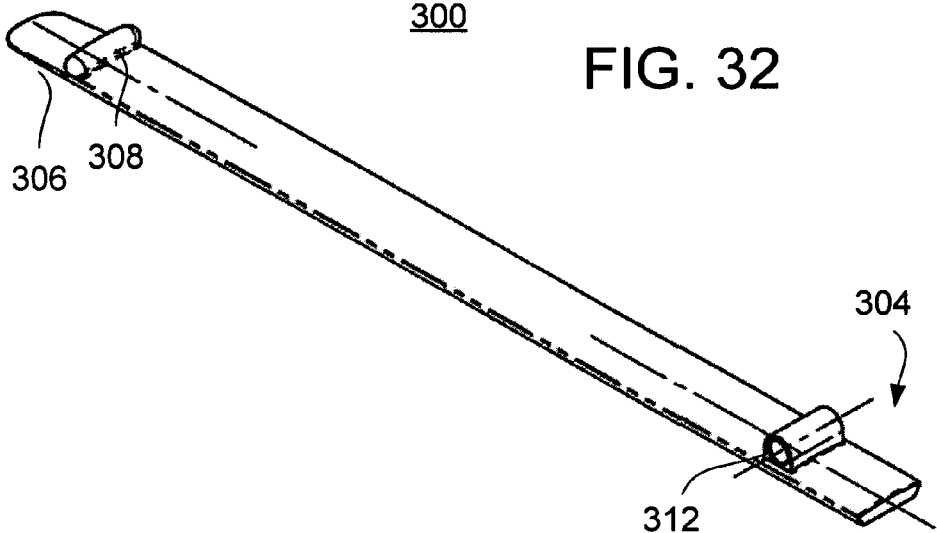
FIG. 32 is a perspective view of a wedge ramp insertion tool suitable for assisting in the implantation of one or more of the intervertebral stabilizers discussed herein.
Figure 33:
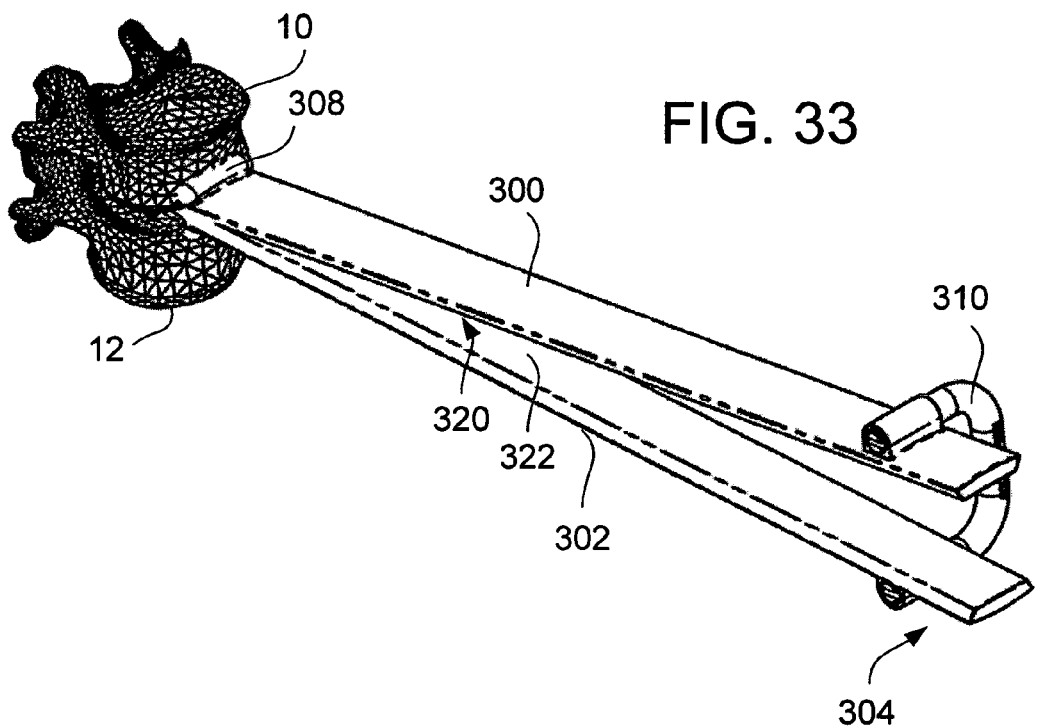

Reference is now made to FIGS. 32 and 33, which illustrate a further insertion tool for implantation of the intervertebral stabilizer 100 from an anterior direction. Again, for purposes of discussion, reference to the stabilizer 100 of FIGS. 6-8 will be made, it being understood that the description may be applied to the other stabilizer embodiments contemplated herein. The insertion tool preferably includes first and second elongate ramps 300, 302 that cooperate to assist in the implantation of the stabilizer 100 into the intervertebral space. A single ramp 300 is shown in FIG. 32, it being understood that the ramp 302 is substantially similar as will be evident to one of ordinary skill in the art after reviewing this specification. Each elongate ramp 300, 302 includes a proximal end 304 and a distal end 306. The distal end 306 is sized and shaped for insertion into the intervertebral space in order to engage one of the end plates. The end 306 preferably includes a stop member 308 that is operable to engage the associated intervertebral bone and to limit a distance that the distal end 306 may enter into the intervertebral space. As best seen in FIG. 33, the stop 308 abuts the vertebral bone 10.

In use, the first and second ramps 300, 302 are disposed opposite to one another to define upper and lower surfaces 320, 322 when the distal ends 306 thereof are inserted into the intervertebral space. The proximal ends 304 of the ramps 300, 302 are preferably fixed positionally with respect to one another by a clamp member 310. More particularly, each of the distal ends 304 includes a bore 312 into which an end of the clamp 310 may be inserted. The clamp 310 is preferably of a U-shape in order to fix the relative positions of the proximal ends 304 with respect to one another. It is noted that the surgeon may omit use of the clamp if he or she insures that the proximal ends 304 of the ramps 300, 302 are fixed with respect to one another by clamping same with his or her hand.

With reference to FIGS. 34 and 35, the intervertebral stabilizer 100 is preferably slid along the surfaces 320, 322 from the proximal end 304 toward the distal end 306. In a preferred embodiment, respective protrusions, such as spikes 121 are spaced apart on at least one of the upper and lower surface 102, 104 of the stabilizer 100 at a distance to accommodate a width of the ramps 300, 302. Advantageously, slideable engagement of the spikes 121 with respective lateral edges 324, 326 of the ramps 300, 302 insure that the stabilizer 100 slides properly along the surfaces 320, 322 and remains between the ramps 300, 302. Preferably, the lateral edges 324, 326 are chamfered in an appropriate way to complement the contour of the spikes 121 to improve slideability and/or stability of the intervertebral stabilizer 100 as it slides along the ramps 300, 302.

As best seen in FIG. 35, the substantially fixed positions of the distal ends 304 of the ramps 300, 302 and the sliding intervertebral stabilizer 100 at least opens the intervertebral space owing to the lever action of the ramps 300, 302. It is also preferred that simultaneously with the opening of the intervertebral space, the intervertebral stabilizer 100 is compressed. It is noted that if the surgeon chooses to manually urge the distal ends 304 of the ramps 300, 302 together while the intervertebral stabilizer 100 is interposed between the proximal and distal ends 304, 306 of the ramps 300, 302, then additional opening of the intervertebral space and/or compression of the intervertebral stabilizer 100 may be obtained. Of course, the surgeon would have to perform this manual operation without the clamp 310.

Figure 36:
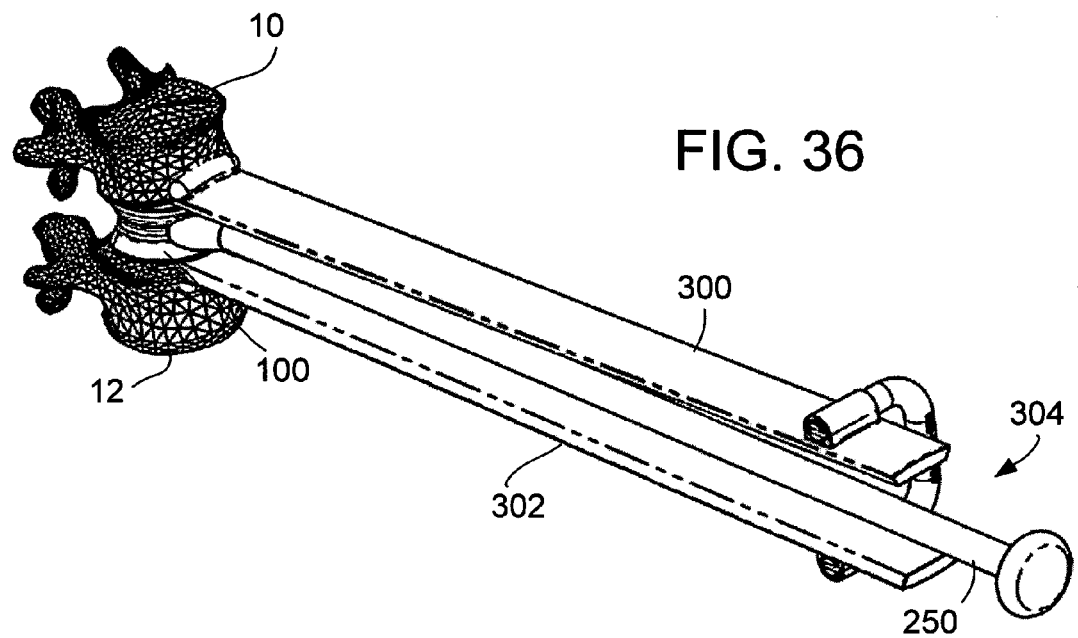
Figure 37:
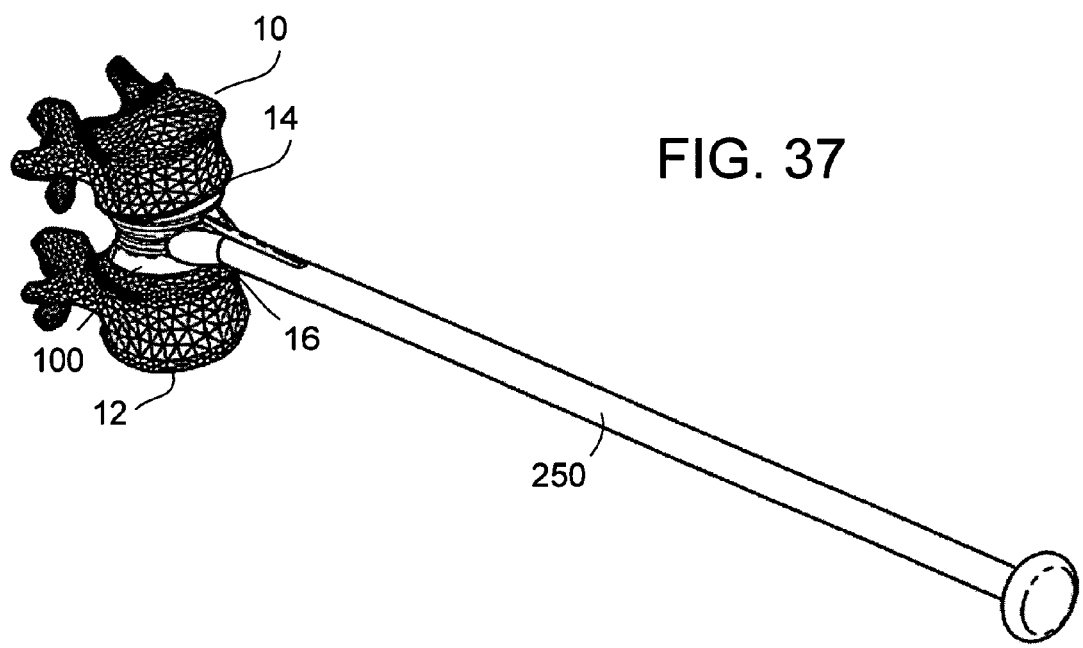

As best seen in FIG. 36, appropriate sliding of the intervertebral stabilizer 100 along the ramps 300, 302 utilizing the handle 252 of the insertion tool 250 results in proper positioning of the intervertebral stabilizer 100 within the intervertebral space. Thereafter, the ramps 300, 302 may be removed such that the intervertebral stabilizer 100 engages the respective end plates 14, 16 of the adjacent vertebral bones 10, 12. Thereafter, the surgeon may remove the insertion tool 250 thereby completing the implantation of the intervertebral stabilizer 100 into the intervertebral space. Appropriate closure procedures may then be carried out.

Figure 38:
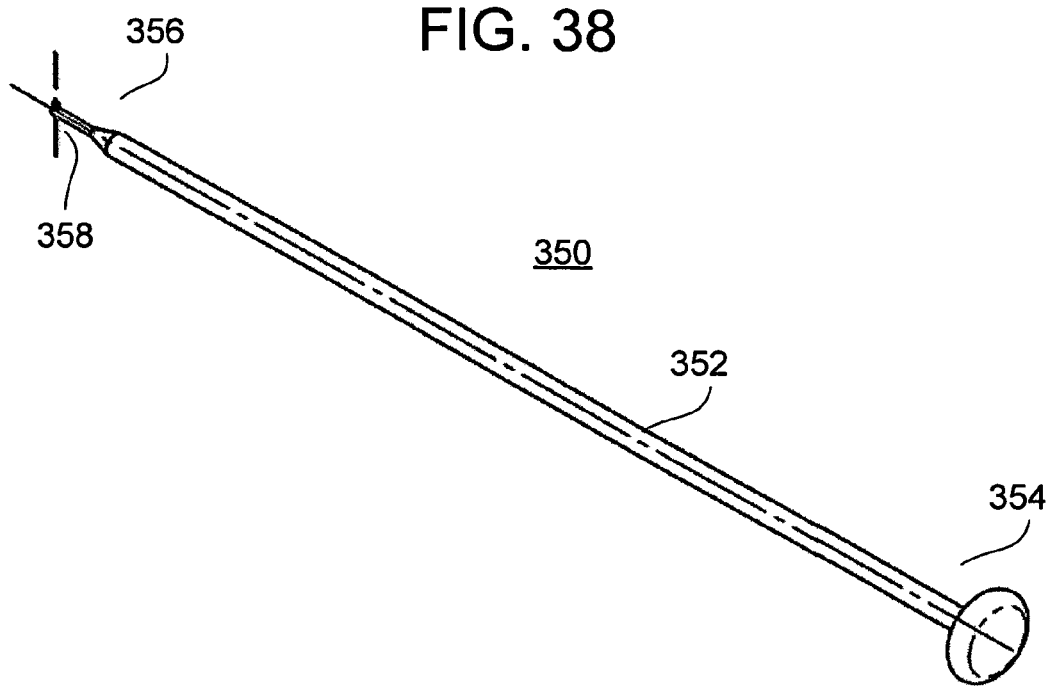
FIGS. 38-39 illustrate perspective and side views of an extraction tool suitable for repositioning and/or extracting one or more of the intervertebral stabilizers discussed herein.
Figure 39:
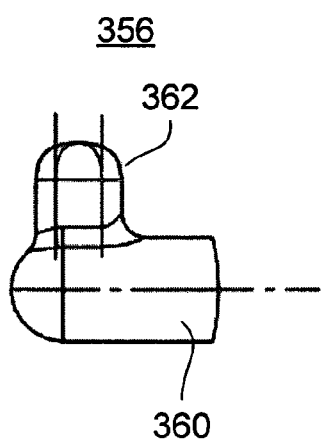

With reference to FIGS. 38 and 39, the surgeon may extract and/or reposition the intervertebral stabilizer 100 after implantation into the intervertebral space. In this regard, an extractor 350 may be utilized. The extractor 350 preferably includes a handle 352 having proximal and distal ends 354, 356, respectively. The extraction tool 350 preferably further includes an engagement element 358 depending from the proximal end 356. The engagement element 358 is preferably operable to releaseably engage the stabilizer 100 after it has been positioned within the intervertebral space. More particularly, the engagement element includes a longitudinally extending member 360 and a transversely extending member 362. The longitudinally extending member 360 is preferably sized such that is may pass through one or more of the apertures 150, 152 (or any of the other aperture embodiments herein). The transversely extending member 362 is preferably sized to pass through the slit 108 as the longitudinally extending member 360 is inserted into the aperture, for example, aperture 150. The longitudinally extending member 360 is preferably of sufficient length to cause the transversely extending member 362 to enter the hollow portion 120 of the body 106. Thereafter, the surgeon preferably rotates the handle 352 of the extraction tool 350 such that the transversely extending member 362 engages an interior surface of the hollow portion 120 such that the stabilizer 100 may be pulled by the handle 352 of the extraction tool 350.

In an alternative embodiment, the engagement element 358 includes a threaded portion (not shown) that may be screwed into a threaded aperture in order to engage the stabilizer. For example, the aperture 158 (FIG. 15) of the stabilizer element 100B may be threaded and the engagement element 358 of the extraction tool 350 may be threaded into the aperture 158 to permit the surgeon to reposition and/or extract the stabilizer element 100B.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A lumbar intervertebral stabilizer for a lumbar region of a spine, comprising:
   a first surface operable to engage an endplate of a first vertebral bone of a spine;
   a second surface spaced apart from the first surface and operable to engage an endplate of an adjacent second vertebral bone of the spine; and
   a spring element including a substantially solid exterior wall forming a hollow passage between the first and second surfaces, the solid exterior wall including at least one helical slit therethrough forming a plurality of annular circumferential, overlapping helical coils, the spring element being disposed between the first and second surfaces and operable to provide reactive force in response to compression loads from the first and second vertebral bones, wherein
   at least some diameters of respective turns of the helical coils differ such that those of the turns having larger diameters are disposed towards the first and second surfaces and those of the turns having smaller diameters are centrally located between the turns having larger diameters, and
   diameters of the hollow passage between the first and second surfaces vary such that larger diameters are disposed towards the first and second surfaces and smaller diameters are centrally located.

2. The lumbar intervertebral stabilizer of claim 1, wherein the spring element includes one of (i) about 1.0 coils; (ii) about 2.0 coils; and about 3.0 coils; and about 4.0 coils.

3. The lumbar intervertebral stabilizer of claim 2, wherein a height between the first and second surfaces is one of: (i) about 7.0 mm to 10.0 mm when the spring element includes about 1.5 grooves or 2.5 coils; (ii) about 10.0 mm to 14.0 mm when the spring element includes about 2.0 groves or 3.0 coils; and (iii) about 14.0 mm to 18.0 mm when the spring element includes about 3.0 groves or 4.0 coils.

4. The lumbar intervertebral stabilizer of claim 3, wherein it is sized and shaped for an intervertebral space in the lumbar region of a spine.

5. The lumbar intervertebral stabilizer of claim 1, wherein a cross-sectional profile taken through the spring element is at least partially hourglass shaped.

6. The lumbar intervertebral stabilizer of claim 5, wherein the cross-sectional profile taken through the spring element has a multiple hourglass shape.

7. The lumbar intervertebral stabilizer of claim 1, wherein at least one of:
   the first surface includes a peripheral edge that overhangs at least one coil of the spring element; and
   the second surface includes a peripheral edge that overhangs at least one coil of the spring element.

8. The lumbar intervertebral stabilizer of claim 7, wherein at least one of:
   a first moment arm is defined by a lateral distance between an outer surface of the at least one coil of the spring element and the peripheral edge of the first surface; and
   a second moment arm is defined by a lateral distance between the outer surface of the at least one coil of the spring element and the peripheral edge of the second surface.

9. The lumbar intervertebral stabilizer of claim 8, wherein at least one of the moment arms defined by the hourglass shape operates such that:
   a compressive force acting on one of the peripheral edges and the other of the first and second surfaces tends to collapse the spring element and full compression of the spring element in response to the compressive force results in adjacent coils engaging one another; and
   further compressive force acting on only a portion of the peripheral edge tends to cause the adjacent coils to engage one another and to expand portions of coils on an opposite side of the spring element from the engaged coils.

10. The lumbar intervertebral stabilizer of claim 1, further comprising:
    at least a pair of apertures extending at least partially into the hollow body and being operable to receive an insertion tool for implanting the stabilizer into a patient, wherein a longitudinal axis of the stabilizer is normal to the first and second surfaces and the apertures extend transverse to the longitudinal axis.

11. The lumbar intervertebral stabilizer of claim 10, wherein the at least one pair of apertures are disposed on an anteriorly directed side of the hollow body.

12. The lumbar intervertebral stabilizer of claim 10, wherein the first and second apertures are longitudinally positioned such that they are entirely within the hollow body and define a closed interior surface.

13. The lumbar intervertebral stabilizer of claim 10, wherein the at least one pair of apertures are longitudinally spaced apart such that a first aperture of the pair is disposed toward the first surface and a second aperture of the pair is disposed toward the second surface.

14. The lumbar intervertebral stabilizer of claim 13, wherein one end of the slit terminates at the first aperture of the pair and an opposite end of the slit terminates at the second aperture.

15. The lumbar intervertebral stabilizer of claim 1, further comprising one or more bone adhesion facilitating elements operable to promote bone adhesion to at least one of the first and second surfaces, wherein the one or more bone adhesion facilitating elements includes at least one of:

one or more spikes extending from at least one of the first and second surfaces for promoting engagement thereof with the associated vertebral bones;

one or more keels extending from at least one of the first and second surfaces for promoting engagement thereof with the associated vertebral bones; and one or more roughening elements one at least one of the first and second surfaces for promoting engagement thereof with the associated vertebral bones.

16. The lumbar intervertebral stabilizer of claim 1, wherein:

the first surface includes a peripheral edge that overhangs at least one coil of the spring element;

a moment arm is defined by a lateral distance between an outer surface of the at least one coil of the spring element and the peripheral edge of the first surface; and the passage is sized and shaped to maximize a length of the moment arm.

17. The lumbar intervertebral stabilizer of claim 16, further comprising a membrane disposed in the passage and substantially closing off the passage to inhibit bone growth therethrough.

18. The lumbar intervertebral stabilizer of claim 17, wherein the membrane is formed as an integral element of the hollow body.

* * * * *